US006458157B1

(12) United States Patent
Suaning

(10) Patent No.: US 6,458,157 B1
(45) Date of Patent: Oct. 1, 2002

(54) RETINAL STIMULATOR

(76) Inventor: Gregg Jørgen Suaning, 89 Gilda Drive, Narara NSW 2250 (AU)

(*) Notice: Subject to any disclaimer, the term of this patent is extended or adjusted under 35 U.S.C. 154(b) by 0 days.

(21) Appl. No.: 09/123,995

(22) Filed: Jul. 29, 1998

Related U.S. Application Data

(60) Provisional application No. 60/061,406, filed on Aug. 4, 1997.

(51) Int. Cl.⁷ .................................................. A61F 2/16
(52) U.S. Cl. ..................................................... 623/6.63
(58) Field of Search ............................. 607/53, 54, 116, 607/148, 149; 623/4, 4.1, 6.63; 128/898, 899; 600/554, 558, 559

(56) References Cited

U.S. PATENT DOCUMENTS

| | | | |
|---|---|---|---|
| 2,760,483 A | * | 8/1956 | Tassicker |
| 3,727,616 A | * | 4/1973 | Lenzkes |
| 3,924,641 A | * | 12/1975 | Weiss |
| 4,408,608 A | * | 10/1983 | Daly |
| 4,419,995 A | * | 12/1983 | Hochmair et al. |
| 4,494,545 A | * | 1/1985 | Slocum et al. |
| 4,532,930 A | * | 8/1985 | Crosby et al. |
| 4,592,359 A | * | 6/1986 | Galbraith |
| 4,628,933 A | * | 12/1986 | Michaelson |
| 4,681,111 A | * | 7/1987 | Silvian |
| 5,109,844 A | * | 5/1992 | De Juan, Jr. et al. |
| 5,324,316 A | * | 6/1994 | Schulman et al. |
| 5,556,423 A | * | 9/1996 | Chow et al. ................. 607/54 |
| 5,865,839 A | * | 2/1999 | Doorish ......................... 623/4 |
| 5,895,415 A | * | 4/1999 | Chow et al. ................. 607/54 |

OTHER PUBLICATIONS

Shandurina et al, "Evoked Potentials to Contact Electrical Stimulation of the Optic Nerves," translated from *Fiziologiya Cheloveka*, 12:16–24 (1986).

Schmidt et al., "Feasibility of a Visual Prosthesis for the Blind Based on Intracortical Microstimulation of the Visual Cortex," *Brain*, 119:507–522 (1996).

Hochmair et al., "An Implanted Auditory Eight Channel Stimulator for the Deaf," *Med. & Biol. Eng. & Comput.*, 19:141–148 (1981).

(List continued on next page.)

*Primary Examiner*—George Manuel
(74) *Attorney, Agent, or Firm*—Alston & Bird LLP

(57) ABSTRACT

An apparatus facilitating the delivery of electrical stimulation to physiologically excitable retinal nerve cells includes: (a), a receiver/decoder/stimulator comprising a semiconductor integrated circuit and other components hermetically sealed within a capsule, implanted and fixed within the eye of the patient such that it may receive power, and decode information from (b), an externally worn image processor/encoder/transmitter comprising an image detector, an image processor capable of translating the image into an array of discreet pixels of varying intensity, encoding the pixel information into a series of discreet data bursts representing the chosen current amplitude, pulse duration, stimulating electrode or electrodes, and reference electrode or electrodes, and transmitting this data to the receiver/decoder/stimulator through a tuned, inductive communication link such that the system may deliver controlled, charge balanced, diphasic, constant current stimulus pulses to (c), discreet metallic electrodes on a flexible, multiple site electrode array implanted on, near or under the surface of the retina. The apparatus provides for flexibility in the external image processing system such that future advancements in processing techniques shall not require revision surgery or modification to the implanted receiver/decoder/stimulator. Safeguards to protect the patient from the delivery of inappropriate stimulus are incorporated into the apparatus, and a method of external collection of diagnostic data from the implanted receiver/decoder/stimulator is described.

20 Claims, 13 Drawing Sheets

OTHER PUBLICATIONS

Normann, "Visual Neuroprosthetics—Functional Vision for the Blind," *IEEE Engineering in Medicine and Biology*, pp. 77–83 (Jan./Feb. 1995).

Normann et al., "Cortical Implants for the Blind," *IEEE Spectrum*, pp. 54–57 (May 1996).

Narayanan et al., "Development of a Silicon Retinal Implant: Cortical Evoked Potentials Following Focal Stimulation of the Rabbit Retina with Light and Electricity," *Investigative Ophthalmology & Visual Science*, 35:592—40 (1994).

Wyatt et al., "Development of a Silicon Retinal Implant: Epiretinal Stimulation of Retinal Ganglion Cells in the Rabbit," *Investigative Ophthalmology & Visual Science*, 35:593—41 (1994).

Wyatt et al., "Ocular Implants for the Blind," *IEEE Spectrum*, pp. 47–53 (May 1996).

Humayun et al., "Bipolar Surface Electrical Stimulation of the Vertebrate Retina," *Arch. Ophthalmol*, 112:110–116 (1994).

Humayun et al., "Visual Perception Elicited by Electrical Stimulation of Retina in Blind Humans,"*Arch. Ophthalmol.*, 114:40–46 (1996).

de Juan, Jr., et al., "Mechanical Retinal Fixation Using Tacks," *Ophthalmology*, 94:337–340 (1987).

Brindley et al., "The Sensations Produced by Electrical Stimulation for the Visual Cortex,"*J. Physiol.*, 196:479–493 (1968).

Donaldson et al., "Experimental Visual Prosthesis," *Proc. IEE*, 120:281–298 (1973).

Dobelle et al., "Phosphenes Produced by Electrical Stimulation of Human Occipital Cortex, and their Application to the Development of a Prosthesis for the Blind," *J. Physiol*, 243:553–576 (1974).

Dobelle et al., "Artificial Vision for the Blind: Electrical Stimulation of Visual Cortex Offers Hope for a Functional Prosthesis," *Science*, pp. 440–443 (Feb. 1974).

Brummer et al., "Electrochemical Considerations for the Safe Electrical Stimulation of the Nervous System with Platinum Electrodes," *IEEE Transactions on Biomedical Engineering*, pp. 59–63 (Jan. 1977).

\* cited by examiner

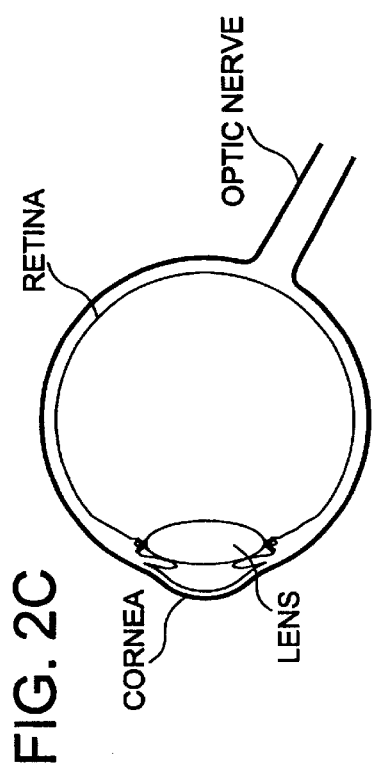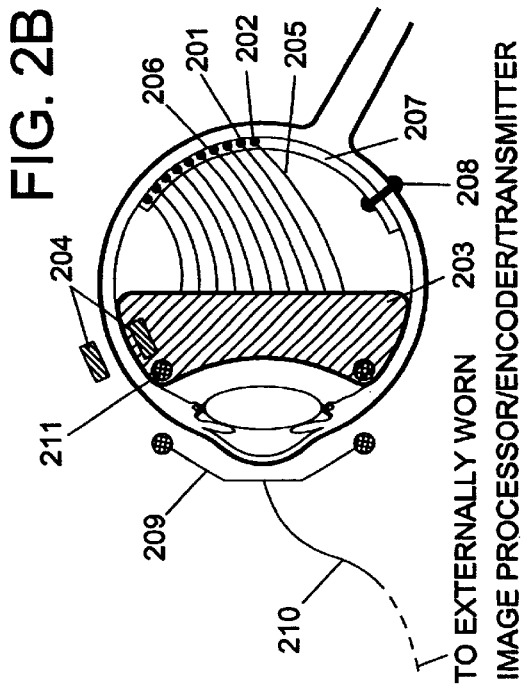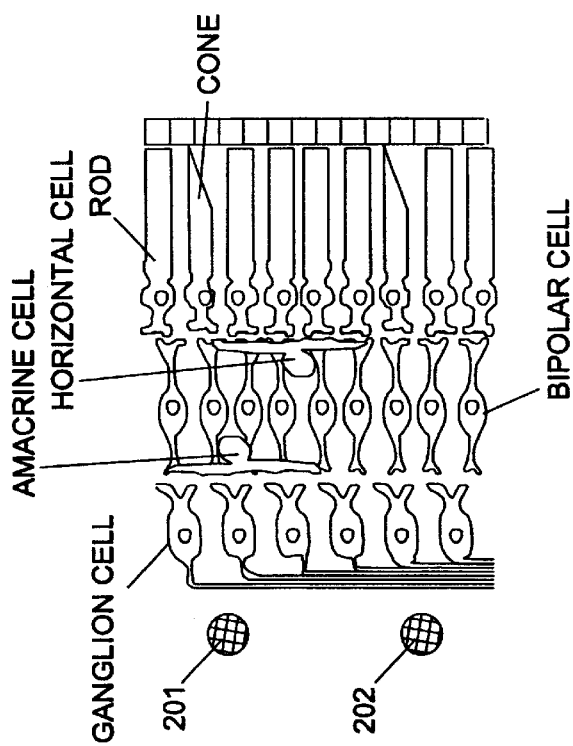

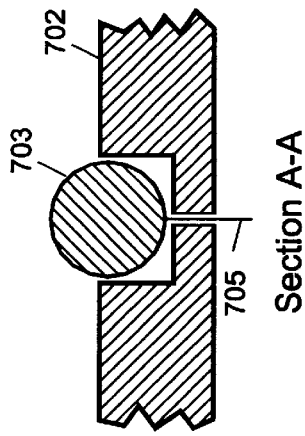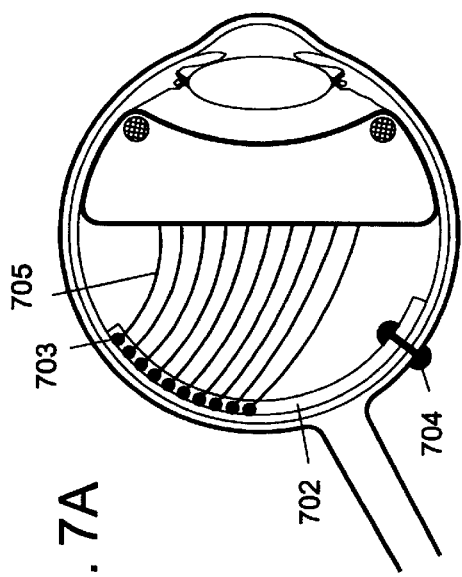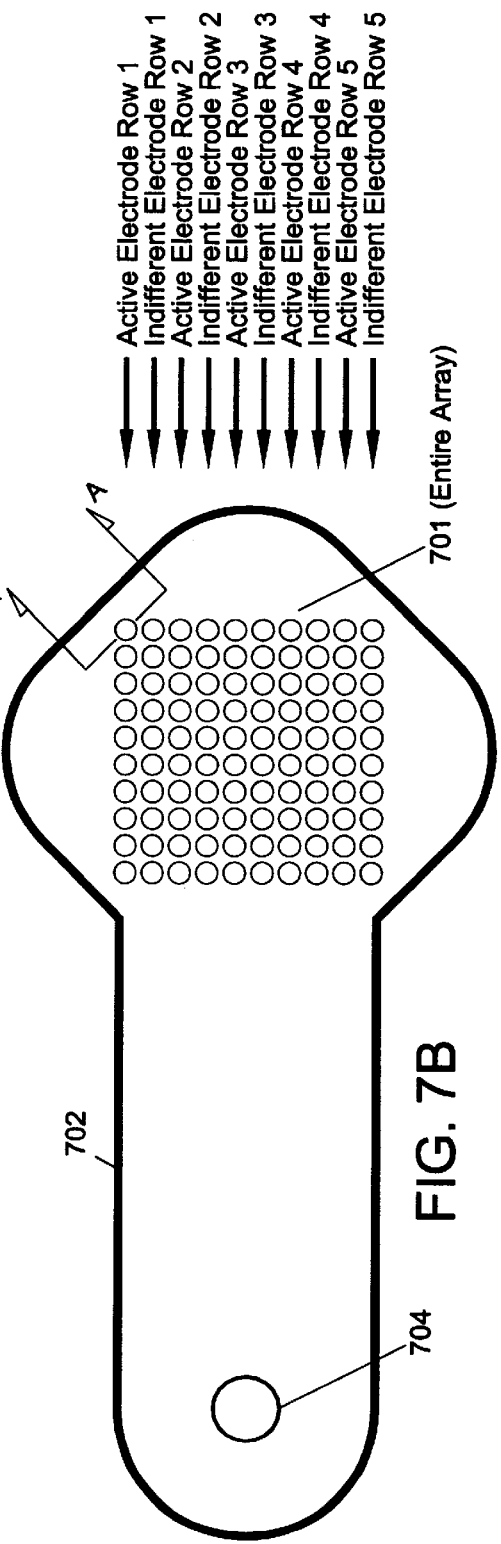

FIG. 9(2)
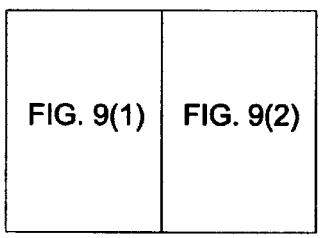
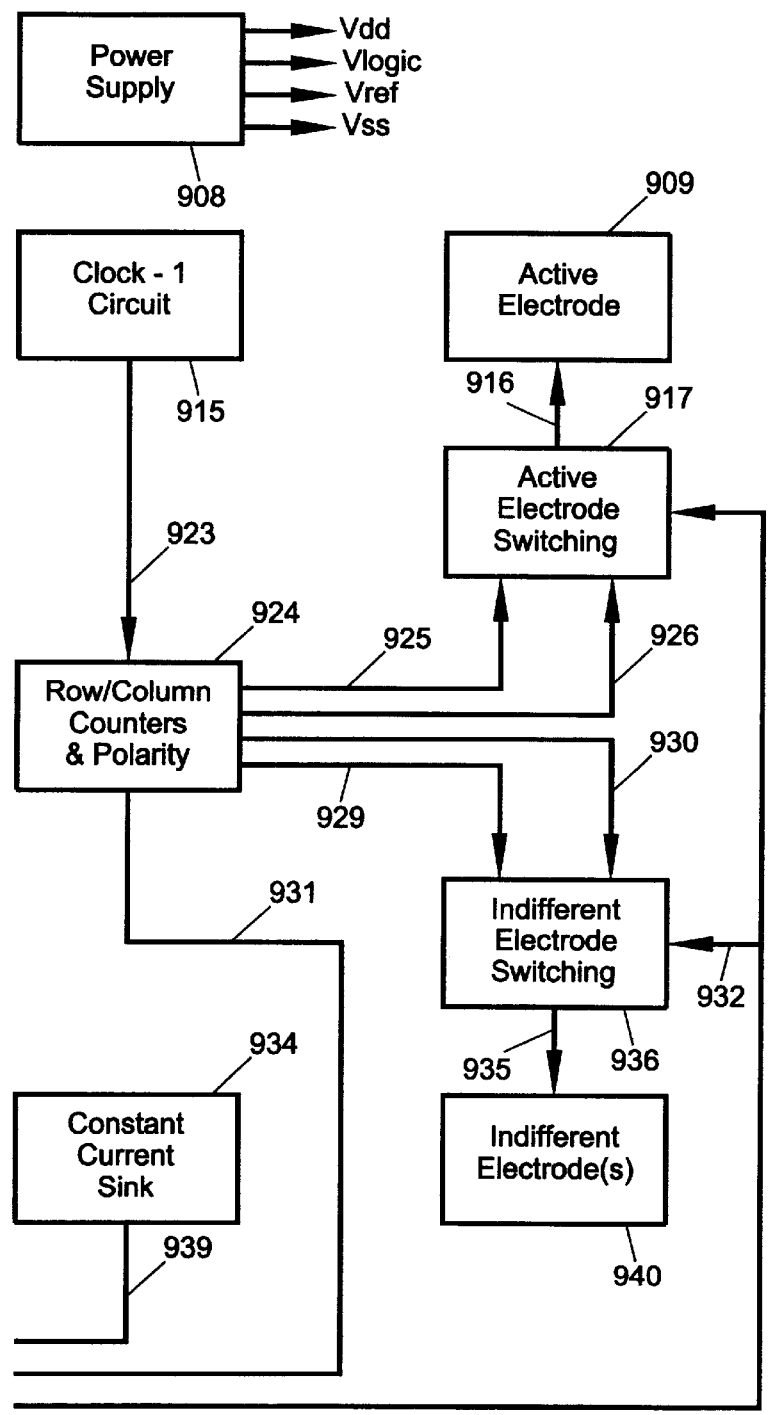

RETINAL STIMULATOR

RELATED APPLICATION

The present application claims priority under 35 U.S.C. § 119(e) to Provisional Application No. 60/061,406, filed Aug. 4, 1997.

FIELD OF THE INVENTION

The present invention concerns an apparatus for electrical stimulation of physiologically excitable retinal nerve cells.

BACKGROUND OF THE INVENTION

The invention described is primarily for an implantable retinal stimulator or visual prosthesis or bionic eye or artificial eye. That is, a system of components designed for the restoration of some visual faculties to the profoundly blind or severely vision impaired. The main objectives of the invention is to restore the differentiation between light and dark and to offer some visual input from the environment.

In many patients who are blinded by degenerative conditions whereby the photoreceptors of the retina become dysfunctional, the retinal ganglion cells can remain largely in tact. It is the objective of the retinal -stimulator to by-pass the dysfunctional photoreceptors and electronically stimulate the surviving retinal ganglion cells, eventuating the perception of a spot of light or phosphene within the brain.

The invention described herein comprises an implanted receiver/decoder/stimulator connected to a multi site electrode array implanted on, near or under the surface of the retina. Through a tuned, inductive communication circuit, power and configuration data for the receiver/stimulator is obtained from an externally worn image processor/encoder/transmitter wherein images from the environment are obtained and processed into a grid of discreet sites of varying intensity and corresponding to the electrode sites of the array. Said intensities are then scaled in stimulus charge (amplitude x duration) in accordance with the individual patient comfort parameters such that the stimulus will be both useful, painless, and safe.

Understanding of the invention will be improved by an understanding of some of the anatomy and physiology of the human eye.

STRUCTURE OF THE HUMAN EYE

The majority of the human eye is protected within the orbital cavity. The exposed section is protected in a limited fashion by various appendages such as the eyelids and brow. Surrounded by the capsule of Tenon, a thin membrane which provides isolation and facilitates movement, the eyeball is embedded within the fatty media of the orbit.

The form of the globe itself is maintained by a hard, dense and unyielding fibrous membrane called the Sclerotic Coat (sclera). Its anterior surface is covered by the Conjunctiva, a membrane which provides the white colouring and is reflected to line the inner surface of the eyelids.

Forming approximately 15% of the anterior of the globe, the Cornea is a transparent quad layer structure consisting of epithelial cells (continuous with the conjunctiva), a central fibrous structure (Substantia Propria), an elastic lamina, and endothelial cells which line the anterior chamber. The cornea is a non vascular structure and is continuous with the sclera.

Approximately 85% of the posterior of the globe is comprised by the Choroid. A thin, highly vascular membrane, the choroid is loosely connected externally to the sclera and internally to the retina. At the point of exit of the optic nerve, the choroid is relatively thick in comparison to other sections and is firmly adhered to the sclera.

The Ciliary Body is comprised of the orbiculus ciliaris, ciliary processes and the ciliary muscle. It is primarily involved with the formation of aqueous humour and in adjusting the eye to the vision of near objects (accommodation).

The orbiculus ciliaris is continuous with the choroid. It is comprised of ridges which are arranged radially and is on the order of four millimetres in width.

The ciliary processes vary between 60 and 80 in number and are similar in structure to the choroid with the exception being that the vessels are larger and are primarily longitudinal in direction.

The ciliary muscle consists of two sets of fibres, circular and radial. By drawing upon the ciliary processes, this muscle contracts and thus relaxes the suspensory ligament of the lens causing the anterior surface of the lens to become more convex.

The Iris, (Latin for rainbow) so named from the various colours observed in different individuals, is a circular curtain which is suspended within the aqueous humour immediately behind the cornea. At its centre (slightly nasal to be precise) is the pupil, a circular aperture for the transmission of light, which changes in size with contractions of the iris. The circumference of the iris is continuous with the ciliary body and is connected to the cornea's elastic lamina by ligament.

The retina forms the interior surface of the eye from the fovea centralis which corresponds with the axis of the eye to the ora serrata near the ciliary body.

A highly complex structure, the retina consists of ten layers between the choroid at its outer surface and the vitreous humour at its inner surface. The ten layers are as follows:

Membrana limitans interna—the most internal layer, comprised of fibres known as the fibres of Muller.

Stratum opticum—a layer of nerve fibres formed by the expansion of the optic nerve.

Ganglionic layer—a single layer of retinal ganglion cells.

Inner molecular layer—a dense layer of fibrils which are interlaced with the dendrites of the ganglion cells and those of the inner nuclear layer (described below).

Inner nuclear layer—comprised of amnacrine, bipolar and horizontal cells.

Outer molecular layer—a dense layer (thinner than the inner molecular layer) of fibrils interlaced with the processes of the horizontal and bipolar cells of the previous layer and the bases of the rods and cones (described below).

Outer nuclear layer—comprised of clear oval nuclear bodies named the rod-granules and cone-granules. Rod-granules being the more populous.

Membrana limitans externa—similar to that of the membrana limitans interna, this layer is also comprised of fibres of Müller.

Jacob's Membrane—the layer of rods and cones. These are the photoreceptors and will be described in more detail later.

Tapetum nigrum—a single layer of hexagonal epithelial cells containing pigment-granules.

Optical or Refracting Media:

Little more than water (with some small amounts of Na and Cl), aqueous humour fills the anterior chamber (bounded by the back of the cornea and the front of the iris) and the posterior chamber (bounded by the back of the iris, the ciliary body and the lens) of the eye.

Filling approximately 80% of the volume of the eye, the vitreous body is perfectly transparent. Bound within a thin and delicate membrane (membrana hyaloidea), the vitreous body is believed to be comprised of numerous laminations of nearly pure water with small amounts of salts and albumen. It is bounded by the retina, the ciliary body and the lens.

The lens is a transparent body consisting of concentric layers ranging from soft on the surface to firm towards the centre. Surrounded by a brittle but highly elastic membrane, the lens is approximately 10 mm in diameter and 4 mm in thickness.

PHYSIOLOGY OF THE HUMAN EYE

The function of the non-retinal components of the ocular anatomy is to maintain a focused, clear image of visual stimuli fixed on the surface of the retina. As the mechanisms involved in this process are analogous to that of a photographic camera, comparisons shall be made for illustrative purposes.

Light enters the eye at the anterior surface of the cornea. It acts in much the same way as the lens of a photographic camera. Approximately two-thirds of the bending of light necessary for providing focus takes place at the air-cornea interface.

Richly supplied with nerves, the cornea is highly sensitive to touch and pain. Its cleanliness is maintained by the tear gland secretion of lubricating fluid which is swept across the surface by the eyelids. This cleaning mechanism is amplified by the presence of dust particles or other foreign objects whereby a reflex leads to blinking and the secretion of additional lubricant.

While the lens provides light bending power in addition to the cornea, its primary role is distance compensation required to maintain focus on the retinal surface. Similar to adjusting focus of a camera by changing the distance between the lens and the film, the ocular lens changes shape, more spherical for near objects, flatter for far ones, by contraction or relaxation of the ciliary muscles. The control of the ciliary muscles is a reflex dependent upon visual input and is related to the reflex which controls the synchronous turning of the eyes.

To maintain proper exposure on the film, the aperture of the camera is adjusted in size by setting the f-stop. This allows the appropriate amount of light into the camera. as In the eye, this mechanism takes place in the iris. The pupil is adjusted in size by either the contraction of the circular muscle fibres sphincter pupillae, or the tenacity of the radial elastic fibres dilator pupillae.

The human retina is part of the brain. While removed from the brain structure itself in its development, its connection is maintained through the optic nerve.

Capable of discriminating between various wavelengths thus providing recognition of colour; providing useful vision with little more than starlight; and yielding extraordinary accuracy and detail, the retina is a complex and quite unique structure of the central nervous system.

The foregoing detailed anatomical description of the retina notwithstanding, the physiological retina may be divided into three distinct layers: the photoreceptor layer; the intermediate cell layer; and the retinal ganglion layer.

Light passes through the tiered cellular structure of the retina to the photoreceptors (rods and cones) on the Jacob's membrane located in the back of the retina, adjacent to the sclera. While this may appear to be odd as the light must pass (and undergo some distortion) through the foregoing layers in order to reach the photoreceptors, it is believed that the reason for this evolutionary phenomenon is the presence of melanin in the tapetum nigrum. This melanin is required in order to absorb light so that it is not reflected back into the refracting media and to assist in the restoration of the pigment in the receptors which is bleached by light.

The rods, the more numerous of the two types of receptors, provide vision in dim light. They do not respond to bright light. Cones on the other hand, do not respond to dim light but provide colour and fine detail vision.

In the centre of the retina, known as the fovea, only cones exist. While cones exist elsewhere within the retina, this region, approximately 500 microns in diameter, is the location where vision is the most acute.

The intermediate cell layer consists of three types of cells: bipolar, horizontal and amacrine cells. Horizontal cells pass signals from the photoreceptors to the bipolar cells which, either through amacrine cells or directly, pass signals to the retinal ganglia.

At the front of the retina lies the layer of retinal ganglia. The axons of the retinal ganglion cells pass across the surface of the retina and collect at the optic disk where they exit to form the optic nerve.

There are approximately one million retinal ganglion cells in the human eye. In contrast, there are approximately 125 million photoreceptors. This being the case, it is an obvious question to ask how resolution is maintained. At the point of regard (the point on the retina passed by a line through the centre of the eye and the apex of the cornea) there exists a one to one correspondence between photoreceptors and retinal ganglion cells. As the angle from the point of regard increases, the quantity of photoreceptors serviced by a given retinal ganglion cell also increases. This provides a corresponding and progressive loss in resolution and eventually fades to no resolution at the far periphery. By this strategy, the eye maintains high resolution where it is important (at and around the point of regard) and only rudimentary vision at the periphery where resolution is not important.

The mechanism by which photic input to the eye is translated into a perception within the brain is not fully understood. Within the eye itself, however, a cascade of events takes place which eventuates a signal or action potential being transmitted by the retinal ganglion cells, the final product of information processing within the retina, to the vision centers of the brain by way of the optic nerve which is formed collectively by the axons of the retinal ganglion cells. This cascade begins with a change in the electrical potential on the surface of the cell membrane of the photoreceptors in response to photic input of the appropriate wavelength. This change in membrane potential causes a synaptic interaction with adjacent bipolar cells which, following a change in their membrane potential, synapse with the retinal ganglion, eventuating a depolarisation thus creating an action potential along the length of its axon.

Horizontal and amacrine cells act as regulating cells. Horizontal cells enhance contrast for spatial analysis through lateral inhibition at the synapses between the photoreceptors and the bipolar cells. Amacrine cells, while involved in several activities, are thought to regulate synapses between the bipolar cells and the retinal ganglion cells to perform temporal analysis or movement detection.

THERAPEUTIC APPLICATION OF A RETINAL STIMULATOR

In some prevalent medical conditions such as retinitis pigulentosa and age related macular degeneration, the photoreceptors of the retina are rendered dysfunctional. It has been found by histological and psychophysical testing that in most of these cases, the retinal ganglion cells and the remainder of the visual pathway remain viable. It has also been determined by psychophysical testing that electronic stimulation of the retinal ganglion cells provide the patient with the perception of a spot of light or phosphene within the spatial vicinity of the stimulation. Variation in the intensity of the perceived phosphene has been observed through variation of stimulus strength although it is unknown if this is due to variations in activity in the originally stimulated cells or due to more retinal ganglion cells being recruited to generate action potentials. Color discretion as not been reported in electronic stimulation of the retina. This is most likely due to the bypassing of the processing levels which occur normally in the retina and provide the perception of color.

PRIOR ART

The restoration of sight to the blind has been the topic of numerous investigations. As early as 1874 surgeons have been aware that electrical stimulation of the human brain is capable of producing physical or psychophysical effects. Magnetophosphenes were recognised as early as 1896. Foerster's 1929 investigations into electrical stimulation of the occipital poles found that phosphenes could be produced through electrical stimulation.

The prosthetic vision system by Brindley and Lewin in the late 1960's led to the concept of a visual prosthesis becoming widely accepted in the scientific community. In 1967, their system of 80 electrodes was implanted in a female volunteer, aged 52 years who had developed bilateral glaucoma. The electrodes were placed on the visual cortex and stimulated by a series of 80 receivers implanted beneath the pericranium and secured to the skull. A helmet containing 80 transmitters was placed on the head of the volunteer, each transmitter being oriented directly above its respective receiver. By radio frequency transmission, the electrical signals required to produce stimulus were transcutaneously sent via inductive coupling to the internal prosthesis. When a series of radio waves was delivered to one of the 80 receivers, the volunteer was able to see a small spot of white light.

Despite the progress achieved in Brindley and Lewin's studies, the useful quantity of phosphenes remained low. While up to 74 of the 75 electrodes were reported to have generated a phosphene in the apparatus implanted in their second patient (see also U.S. Pat. No. 3,699,970), many of these were too far removed from the point of regard to be useful. Furthermore, the surgery required for implantation was extensive and the apparatus for stimulation large and cumbersome. While not well known at the time, the monophasic nature of the stimulus pulses was likely to cause irreversible electrochemical reactions at the electrode/tissue interface with long term stimulation. Nevertheless, Brindley's second patient was able to identify geometric patterns and read Braille at up to 90% accuracy at a rate of seven letters per minute using the device alone.

The human visual pathway possesses at least four potential sites of neurostimulation; the retina, the optic nerve, the lateral geniculate nucleus and the visual cortex.

While stimulation of the visual cortex has shown promise, practicality remains an issue. Implantation of a cortical prosthesis requires intracranial neurosurgery. A similar argument applies to the lateral geniculate nucleus. Nevertheless, stimulation of the visual cortex or the lateral geniculate nucleus remains the only option for those with damaged optical pathways leading to these higher processing centers.

Access to the optic nerve is readily available and would appear to be a reasonable site for stimulation of the visual pathway. However, the mapping of stimuli is largely undefined.

Relatively simplified access and common surgical techniques, including the use of retinal tacks for fixation, imply that the retina is an appropriate site for placement of a stimulating apparatus.

A number of attempts have been made to restore useful vision through electrical stimulation of physiologically excitable retinal nerve cells.

Michaelson (U.S. Pat. No. 4,628,933) has proposed a system whereby photosensitive diodes or charge coupled devices are used to detect incident light focussed upon the implanted apparatus by the existing refractory media of the eye. A radiofrequency or electromagnetic system of powering the apparatus is employed.

Systems utilizing photodiode receptors powered by incident light focussed upon the device, implanted beneath the retina, have been proposed by Chow (see U.S. Pat. Nos. 5,016,633, 5,024,233, 5,397,350 and 5,556,423). As no functioning devices of this nature have been implanted in humans, the sufficiency of the incident light to generate the energy necessary to elicit a response in the retinal ganglion cells remains in question, as does the monophasic nature of the stimulus generated by photodiodes as this may cause electrode dissolution or nerve damage.

In these systems, and those like them, the processing of the visual image takes place internal to the eye. Thus, no technological changes to the system can be made without revision surgery. It is likely that direct visual images are not the most effective means of utilizing a visual prosthesis as much of the normal processing of images cast upon a functional eye takes place in the lower orders of cells such as the photoreceptor, bipolar, amacrine and horizontal cells which are bypassed by these prostheses. Pre-processing such as edge detection or feature extraction may be necessary in order to utilize a neural stimulator to convey visual information effectively in the absence of the retinal processing mechanisms.

Rizzo and Wyatt (see also Wyatt J, Rizzo J. Ocular implants for the blind. *IEEE Spectrum*; 1996:47–53) have proposed a stimulator chip placed upon a polyimide substrate which is powered and controlled by an external laser beam through a photodiode array (see also Wyatt J, Rizzo J. Ocular implants for the blind. *IEEE Spectrum*; 1996:47–53). Although none have been implanted in humans, this system has good merit but requires a rather sophisticated eye tracking system in order that the laser beam remains fixed on the target photodiode array.

Topographic mapping of stimuli upon the retina is well defined and studies by Humayun et al. (see also Humayun M, Sato Y, Propst R, de Juan E. Can visual evoked potentials be elicited electrically despite severe retinal degeneration and markedly reduced elecroretinogram? *Ger J Ophthalmol*. 1994;4:57–84) found that the ganglion cells are capable of being stimulated by means of electrical signals delivered to the retinal basement membrane.

Humayun, de Juan and their colleagues at Johns Hopkins University have provided results which have confirmed that not only is stimulation of the human retina possible, the capability exists to detect movement and distinguish between adjacent phosphenes. They have gone on to propose a device and estimate the stimulation parameters necessary in eliciting a visual response in human patients (see also U.S. Pat. No. 5,109,844 and Humayun M S, de Juan E, Jr., et al. Visual perception elicited by electrical stimulation of retina in blind humans. *Arch Ophthalmol*. 1996; 114:40–6).

Successful restoration of a human sense has been achieved in the case of cochlear implants. In this instance, the lowest functioning level of the auditory pathway (the cochlea) is stimulated rather than higher levels such as the auditory nerve or the auditory brainstem (see also U.S. Pat. No. 4,419,995 by Hochmair et al. and U.S. Pat. No. 4,532,30 by Crosby et. al.). This suggests that retinal implants which target the lowest remaining functional level of the visual pathway (the retinal ganglion cells) may have similar success in the restoration of vision.

SUMMARY OF THE INVENTION

The primary aim of the invention is to restore visual sensation by electrically stimulating the retinal ganglion cells of the human retina in persons affected by degenerative diseases of the eye which have led to blindness or severe visual impairment.

In view of the absence of chronically implantable retinal stimulators capable of demonstrating effectiveness in the prior art, it is an objective of the present invention to provide a means by which chronic implantation & retinal stimulation may take place.

The present invention, an apparatus facilitating the delivery of electrical stimulation to retinal nerve cells, includes a receiver/decoder/stimulator comprising a semiconductor integrated circuit and other components hermetically sealed within a capsule, implanted and fixed within the eye of the patient such that it may receive power, and decode information from an externally worn image processor/encoder/transmitter through a tuned, inductive communication link and deliver controlled, charge balanced, diphasic, constant current stimulus pulses to discreet metallic electrodes on a flexible, multiple site electrode array implanted on, near or under the surface of the retina.

Said image processor comprises a means of obtaining an image, processing the image into an array of discreet pixels of variable intensity and encoding said pixel information into a series of discreet data bursts, transmitted to the receiver/decoder/stimulator, representing the chosen current amplitude, pulse duration, stimulating electrode or electrodes, and reference electrode or electrodes.

A Radio Frequency (RF) data and power trans-tissue, inductive link between the external image processor/encoder/transmitter and the internal receiver/decoder/stimulator provides for flexibility in the external image processing system such that future enhancements in processing techniques shall not require revision surgery or modification to the implanted receiver/decoder/stimulator and eliminates the need for maintenance of an internal power source such as a battery.

As chronic implantation requires, the apparatus is shaped in such a way as to provide comfort to the patient. All tissue contacting components and those components capable of exposure to tissue by way of leeching, etc. may be fabricated from materials known to be well tolerated by human tissue. Electronic circuitry required to power or control the apparatus is safely encapsulated within a hermetic chamber thereby protecting the patient from tissue-incompatible materials found in modem electronic components in addition to facilitating the presence of electronic circuitry within the corrosive environment of bodily fluids.

The circuitry of the receiver/decoder/stimulator possesses a means of excluding the delivery of a stimulation signal in the event that the encoded information received violates a pre-determined data protocol. This prevents erroneously encoded stimulus pulses from being delivered to the patient.

A common approach of insuring a charged balanced stimulus waveform in neural stimulation is to place a capacitor in series with each electrode such that no net DC current will pass. The present invention, in addition to using balanced, diphasic stimulus waveforms, employs a technique that reduces the quantity of capacitors necessary to insure charge balance from one capacitor per electrode to a total of two capacitors thus significantly reducing the size of the apparatus by reducing the quantity of components.

The apparatus is capable of delivering the aforesaid stimulus waveforms to a plurality of electrode sites. The circuitry of the receiver/decoder/stimulator differentiates the electrodes into two distinct blocks, active and indifferent. The role of these blocks can be transposed by the data sent to the device from the image processor/encoder/transmitter such that stimulus can be delivered by any one electrode in either block and the return path for the electrical signal may be passed through any one or more electrodes in the opposing block.

The apparatus possesses a means, external to the patient, of receiving data from the implanted receiver/decoder/stimulator such that the fall in electrical potential across the stimulation circuit may be derived. This, in addition to the programmable current amplitude shall facilitate the determination of the tissue impedance through which the stimulus has passed.

Maintenance of position of the implanted receiver/decoder/stimulator is, either in whole or in part, achieved by fixation of magnetic material, such as a hermetically sealed, rare earth magnet or ferromagnetic material within the external fatty media which surrounds the eye. Within the receiver/decoder/stimulator exists magnetic material which is attracted to said material in the fatty media thus achieving a mutual attraction between the internal receiver/decoder/stimulator and the material in the fatty media.

BRIEF DESCRIPTION OF THE DRAWINGS

FIG. 2 shows the relevant ocular anatomy and the relative positioning of the receiver/decoder/stimulator within the eye.

FIG. 7 shows the preferred configuration of the stimulating electrode array.

Figure 1:
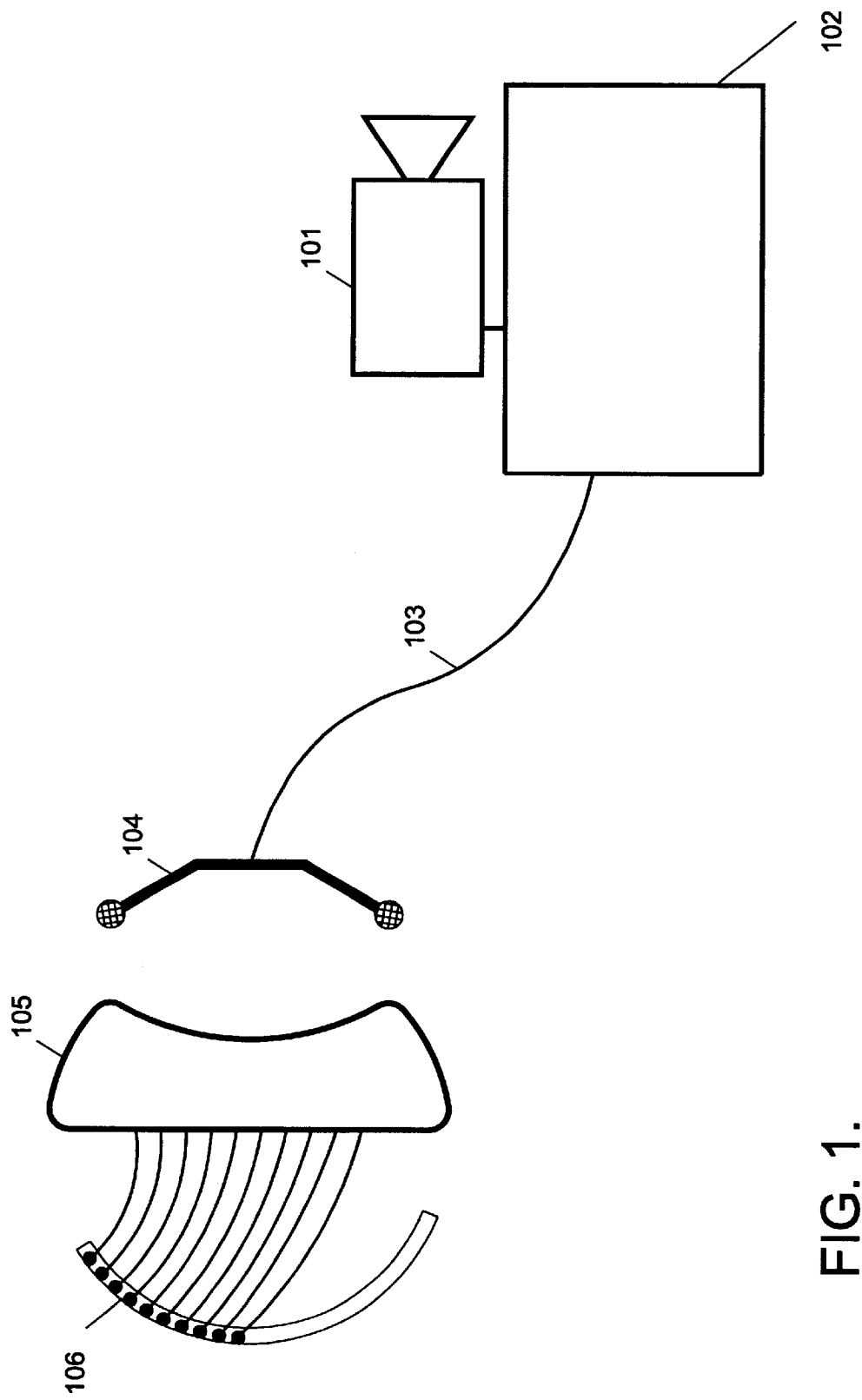
FIG. 1 shows a pictorial representation of the invention.

Identifying numbering of items within drawings associated with the description of the Retinal Stimulator is such that each drawing possesses a unique numbering sequence. As a result, some items in a given drawing may appear on another drawing and be identified by a different number. Where necessary for clarity, text associated with the description of a given drawing makes cross reference to other drawings.

DETAILED DESCRIPTION OF THE PRESENT INVENTION

The method of the present invention, a retinal stimulator, is illustrated in FIGS. 1 through 11.

A retinal stimulator (FIG. 1) comprises an external image detector/processor 101 that supplies encoder/transmitter 102 with image data, said image data is translated into a series of encoded, radiofrequency bursts according to a predetermined protocol and sent to tuned transmitting antenna 104 via cable 103; transmitted radiofrequency waves (not shown) are broadcast from antenna 104, through tissue (not shown), and received and decoded in receiver/decoder/stimulator 105 to extract stimulation parameter data and rectified to power said receiver/decoder/stimulator; in accordance with the decoded data, a controlled, diphasic, charge balanced, constant current stimulus wave is delivered to a single active stimulating electrode on electrode array 106, enters retinal tissue (not shown) and returns through one or more indifferent electrode(s) on 106 and to receiver/decoder/stimulator 105. If specified in the data, the receiver/decoder/stimulator 105 will transmit two distinct energy bursts, related in time to the voltage across its constant current sink and supply voltage respectively at the time of the delivery of stimulus. Said energy bursts are received by external antenna 104 for detection and measurement by an appropriate apparatus such as an oscilloscope.

The physiologically excitable cells shown in FIG. 2A maintain an electro-chemical equilibrium when at rest whereby there is no net exchange of ions across the cell membrane. Upon the arrival of a stimulus pulse from the receiver/decoder/stimulator at a given electrode site (such as 201), cathodic current will pass into the tissue on its way back to the receiver/decoder/stimulator via indifferent electrode(s) (such as 202) in an effort to complete the circuit. Said cathodic current serves to change the electrical potential of the membrane of a given excitable cell, in particular a retinal ganglion cell, by causing voltage gated channels on the cell membrane to change their conductance to particular ions. If sufficient in magnitude, the change in electrical potential between the inside and outside of the cell will evoke an action potential or wave of depolarization which travels the length of the cell axon to higher order neurons of the brain that process vision. Immediately following the cathodic phase of the stimulus pulse, an anodic phase of equal magnitude and duration serves to protect the tissue from potentially damaging electrical charge build-up, and the electrode material from electrochemical dissolution. It is important that the waveform delivered to the active electrode site be cathodic in the first phase as anodic current would serve to hyperpolarize the cell membrane thus making depolarization more difficult to achieve.

The relative locations of the components of the present invention are shown in FIG. 2B. The receiver/decoder/stimulator 203 is located in the proximal hemisphere of the eye and held in place with the assistance of magnetic attractors 204 located both internal and external to the sclera, fixed to the fatty media which surrounds the eye externally and fixed to the receiver/decoder/stimulator 203 internally. The receiver/decoder/stimulator body is a hollow chamber wherein all body incompatible materials are hermetically sealed. The distal hemisphere of the eye, containing all but the periphery of the retina, is the site at which the electrode lead wires (205 and alike) exit the receiver/decoder/stimulator 203 via hermetic feed-through to pass through the vitreous humour to the electrode array 206, collectively formed by electrode carrier 207, electrodes 201, 202 and alike. Said electrode array 206 is fixed to the ocular anatomy by way of appropriate attachment such as Retinal Tack 208. The external image processor/encoder/transmitter is worn by the patient in a convenient location on the body. The transmitter antenna 209 which is connected to the remainder of the electronics via cable 210 is situated in close proximity to the front of the eye such that the transmitted signals can be detected by the internal antenna 211 of the receiver/decoder/stimulator 203.

Figure 3:
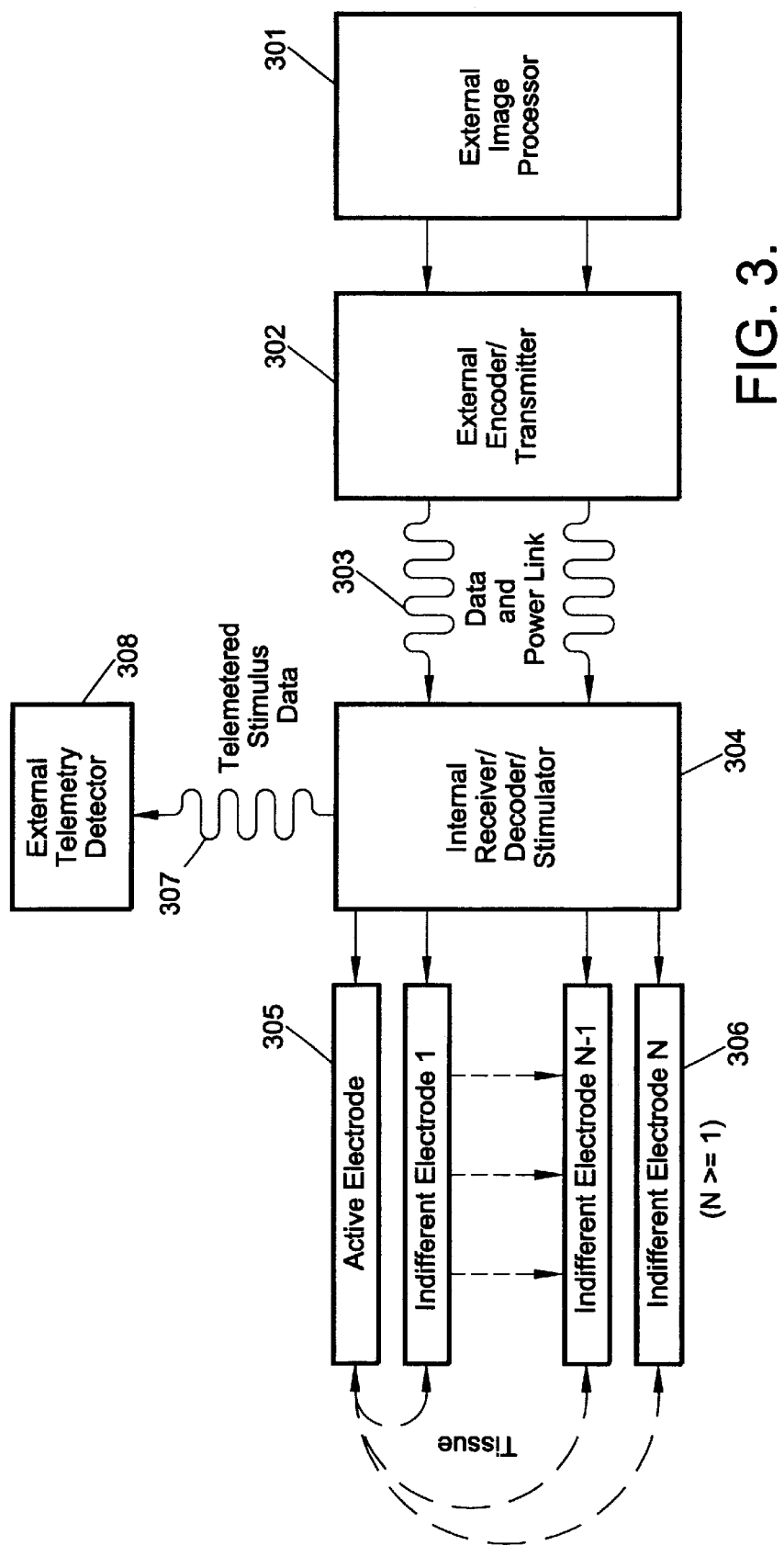
FIG. 3 shows a block diagram for the preferred operation of the apparatus.

General operation of the Retinal Stimulator is shown in diagrammatic form in FIG. 3. The external image processor 301 obtains an image and reduces the data contained in said image to that of an array of pixels of varying intensity. A preferred means of achieving said processing and data reduction is as simple as obtaining a virtual image from a camera and extracting the pixel intensity at discreet sites corresponding to the geometrical pattern of the pixel array using a microprocessor based computer program. The means of image processing should not be considered limited to the preferred method, as it is the variability of the image processing methods which adds to the versatility of the present invention. The external encoder/transmitter 302 comprises software, a microprocessor for execution of said software, a data buss for the transfer of binary data to a burst generation circuit, and a transmitter circuit for the generation of radio waves in encoded bursts (described in detail below). Said radio waves are transmitted from an antenna within 302 (see also 209 of FIG. 2) then passed through the tissue at the front of the eye via Data and Power Link 303 and received by an implanted antenna within Internal Receiver/Decoder/Stimulator 304 (see also 211 of FIG. 2). Said receiver/decoder/stimulator contains electronic circuitry that detects and counts the incoming radio waves of a given burst such that decoding may occur in accordance with a predetermined protocol as described in detail below. At the same time, the radio waves are rectified and used to charge a capacitor which stores and supplies power to the implanted electronic circuitry of 304. During decoding, the circuitry corresponding to the data contained in each respective burst is configured such that the appropriate switches are closed in preparation of sending stimulus to the chosen active electrode 305 and chosen indifferent electrode(s) 306 (and alike). The amplitude burst sets the controlling current input of a current mirror thus setting the current to be passed through the constant current sink. Upon arrival of the burst that initiates and determines the duration of the first phase of stimulus, switches connecting the input to the constant current sink and the positive power supply voltage to the active electrode 305 and indifferent electrode(s) 306 (and alike) respectively are closed such that the cathodic phase of stimulus is delivered from the active electrode 305, to the retinal tissue, and returns through the indifferent electrode(s) 306 (and alike) (see also FIG. 6A). Upon completion of the detection of the phase one burst, the switches connecting the active and indifferent electrodes to the positive power supply and constant current sink are opened. The arrival of the burst that initiates and determines the duration of the second phase of stimulus causes the closure of switches connecting the input to the constant current sink and the positive power supply voltage to the indifferent electrode(s) 306 (and alike) and active electrode 305 respectively such that the anodic phase of stimulus is delivered from the active electrode, to the retinal tissue, and returns through the indifferent electrode(s) (see also FIG. 6B). By extending the silent period between successive stimulus sequences, the receiver/decoder/stimulator 304 will generate two distinct energy bursts, related in time to the voltage at the input of the constant current sink and the power supply voltage respectively during stimulation. Said energy bursts 307 are transmitted by the internal antenna within 304 and received by the external antenna within 302. By measuring the time from the falling edge of the last burst of a given sequence to the detection of each of the aforesaid energy bursts by means of an external telemetry detector 308 such as an oscilloscope or purpose built circuitry, an estimate of the voltage drop across the stimulation circuit during the delivery of stimulus may be obtained. Said voltage drop in conjunction with knowledge of the programmed current amplitude yields an estimate of the impedance across the circuit through which stimulus has passed.

Figure 4:
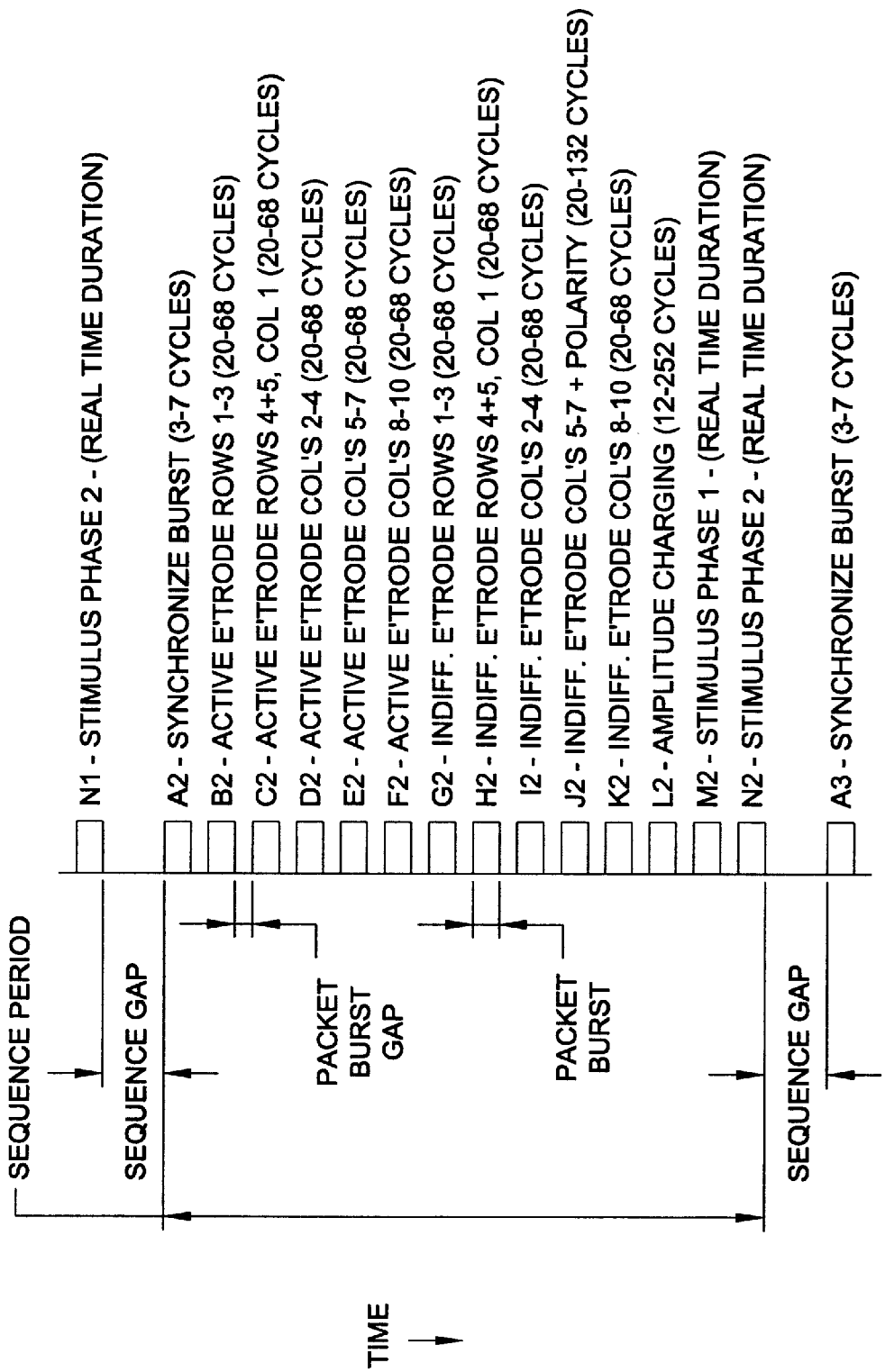
FIG. 4 shows the protocol for data and power transmission.

To insure safe and predictable delivery of stimulus to the retinal tissue, the retinal stimulator employs a predetermined protocol for the data transfer from the external image processor/encoder/transmitter to the internal receiver/decoder/stimulator. A pictorial representation of said protocol is shown in FIG. 4 wherein parts of three sequences are shown:

sequence 1 wherein only the last packet burst is shown (N1)

sequence 2 wherein the entire sequence is shown (A2, B2,C2, . . . ,N2)

sequence 3 wherein only the first packet burst is shown (A3)

A packet burst is defined by the presence of fixed frequency pulses wherein a plurality of said pulses exist. Each packet burst has a beginning and an end whereby fixed carrier frequency pulses commence and cease respectively. Each packet burst is separated in time by a packet burst gap wherein no pulses are present. Packet bursts are translated from logic level (0–5V) signals to radiofrequency (RF) waves prior to broadcast from the image processor/encoder/transmitter by way of an oscillating circuit, tuned to the carrier frequency.

The following description of the protocol shall be given in the context of being received by the receiver/decoder/stimulator where the decoding of said protocol takes place.

Due to the energy build-up and discharge intrinsic to all oscillating circuits, undershoot and ringing will occur at the beginning and end of a given RF packet burst respectively. For this reason, counting the exact quantity of pulses exceeding a given threshold is likely to lead to errors. To eliminate the effects of this phenomenon, a divide by n strategy is employed. This allows some pulses to be below the threshold and provides a facility for tolerance of ringing. The selection of the value of n is dependent upon several factors such as damping, frequency, threshold, etc. As a matter of convenience and functionality, the value of n has been chosen to be 8. By sending 8 RF cycles above a given threshold, the receiver/decoder/stimulator circuit will count the packet burst as: 8/8=1. Since it cannot be guaranteed that all 8 RF cycles are above the detection threshold, an additional 4 cycles are sent to compensate for energy build-up in the oscillating circuit. By sending 12 RF cycles, we exceed the cycles necessary to count a one (12/8=1) but fall short (by 4 RF cycles) of counting a two. Thus, up to three "ringing cycles" and three "undershoot cycles" may be tolerated in a given packet burst. For a plurality of counts to be delivered to the circuit, the following conversion applies:

$$\text{cycles} = 8m + 4 (RF \text{ cycles})$$

Where m is the number of counts to be delivered to the receiving circuit.

Incoming RF cycles are detected by the receiver/decoder/stimulator at two levels:

Packet burst detection

Sequence detection

Upon detection of a packet burst, both detection levels are activated. Upon the completion of said packet burst, the two detection circuits wait for fixed periods of time for additional RF cycles to arrive. Packet burst detection waits for a short period of time—slightly longer than the carrier frequency period. If no further RF cycles arrive within this is time, packet burst detection is inactivated. Sequence detection waits an extended period of time, slightly longer than the maximum prescribed packet burst gap, for additional RF cycles to arrive (ie. the next packet burst). Sequence gaps, being longer than the maximum prescribed packet burst gap, cause the sequence detection circuit to become inactivated. In effect, the packet burst detection is active when a packet burst is being received and sequence detection is active when a sequence is being received.

A given sequence is initiated with a synchronize burst (burst A of FIG. 4), a unique packet burst which alerts the circuit that a sequence is beginning and valid data is to be delivered in subsequent packet bursts. The synchronize burst must be sufficient in duration to activate the packet burst detection circuit but must not have sufficient cycles to trigger a count of one when the cycles delivered are divided by eight. Only by receiving a synchronize burst meeting these conditions will the receiver/decoder/stimulator circuit be enabled for decoding subsequent packet bursts. Detection of cycles in excess of seven for a given synchronize burst shall place the receiver/decoder/stimulator circuit in a state whereby it is inactive until a new, valid synchronize burst arrives.

Each packet burst in the protocol must exist in its respective order for the circuit to decode the data properly and avoid an overflow reset (described below). In the event that a given packet burst is to achieve nothing (does not turn on any electrode rows or columns), the quantity counted by the circuit using the divide by n strategy must be zero. In order to differentiate between a synchronize burst and other packet bursts which are delivered to provide a count of 0 ((8*0)+4=4), the receiver/decoder/stimulator employs a "count minus one" circuit upon the receipt of all packet bursts which specify electrode rows or columns. Thus, the formula for RF cycle quantities in these packet bursts is:

$$\text{cycles} = 8 + (8m + 4)(RF \text{ cycles})$$

For a count of zero to be detected by the receiver/decoder/stimulator in a given packet burst, 12 cycles are sent. This value exceeds that of the synchronize burst but the "count minus one" circuit interprets this as zero counts.

Following each RF packet burst, a "silent" period or packet burst gap is necessary in order to provide a distinct separation of packet bursts and to allow for the packet burst detection circuit to become disabled. Choice of packet burst gap cycle quantity is based upon: the need to deliver sufficient RF to power the implantable electronics, the need to avoid the possibility of overlapping two or more sequential packet bursts and the need to avoid disabling the sequence detection circuit during a sequence. For the purpose of the present description, the duration of the packet burst gap shall be 12 cycles of silence.

The protocol, in sequential order, is described as follows. Where applicable, the remedial action caused by an excess of cycles is described.

BURST A—SYNCHRONIZE BURST: Between 3 and 7 cycles to trigger a packet burst detection but insufficient to count a one (cycles/8). This will enable the circuit for processing of further data. Cycles in excess of the maximum 7 cycles shall reset the circuit and force it to wait for the next synchronize signal.

BURST GAP: 12 RF cycles (not sent).

BURST B—ACTIVE ELECTRODE ROWS 1–3: 20–68 RF cycles to set 3 bits on a binary counter to specify the connection of active electrode rows 1 through 3. Cycles in excess of the maximum 68 cycles shall reset the circuit and force it to wait for the next synchronise signal.

BURST GAP: 12 RF cycles (not sent).

BURST C—ACTIVE ELECTRODE ROWS 4–5/ ACTIVE ELECTRODE COLUMN 1: 20—68 RF cycles to set 3 bits on a binary counter to specify the connection of active electrode rows 4 through 5 and active electrode column 1. Cycles in excess of the maximum 68 cycles shall reset the circuit and force it to wait for the next synchronise signal.

BURST GAP: 12 RF cycles (not sent).

BURST D—ACTIVE ELECTRODE COLUMNS 2–4:20–68 RF cycles to set 3 bits on a binary counter to specify the connection of active electrode columns 2 through 4. Cycles in excess of the maximum 68 cycles shall reset the circuit and force it to wait for the next synchronise signal.

BURST GAP: 12 RF cycles (not sent).

BURST E—ACTIVE ELECTRODE COLUMNS 5–7: 20–68 RF cycles to set 3 bits on a binary counter to specify the connection of active electrode columns 5 through 7. Cycles in excess of the maximum 68 cycles shall reset the circuit and force it to wait for the next synchronise signal.

BURST GAP: 12 RF cycles (not sent).

BURST F—ACTIVE ELECTRODE COLUMNS 8–10: 20–68 RF cycles to set 3 bits on a binary counter to specify the connection of active electrode columns 8 through 10. Cycles in excess of the maximum 68 cycles shall reset the circuit and force it to wait for the next synchronise signal.

BURST GAP: 12 RF cycles (not sent).

BURST G—INDIFFERENT ELECTRODE ROWS 1–3: 20–68 RF cycles to set 3 bits on a binary counter to specify the connection of indifferent electrode rows 1 through 3. Cycles in excess of the maximum 68 cycles shall reset the circuit and force it to wait for the next synchronise signal.

BURST GAP: 12 RF cycles (not sent).

BURST H—INDIFFERENT ELECTRODE ROWS 4–5/ INDIFFERENT ELECTRODE COLUMN 1: 20–68 RF cycles to set 3 bits on a binary counter to specify the connection of indifferent electrode rows 4 through 5 and indifferent electrode column 1. Cycles in excess of the maximum 68 cycles shall reset the circuit and force it to wait for the next synchronise signal.

BURST GAP: 12 RF cycles (not sent).

BURST I—INDIFFERENT ELECTRODE COLUMNS 2—4:20–68 RF cycles to set 3 bits on a binary counter to specify the connection of indifferent electrode columns 2 through 4. Cycles in excess of the maximum 68 cycles shall reset the circuit and force it to wait for the next synchronise signal.

BURST GAP: 12 RF cycles (not sent).

BURST J—INDIFFERENT ELECTRODE COLUMNS 5-7/POLARITY: 20–132 RF cycles to set 4 bits on a binary counter to specify the connection of indifferent electrode columns 5 through 7 and the fourth bit to specify the polarity of the power supply (to facilitate the reversal of the function of the active and indifferent electrodes). Cycles in excess of the maximum 132 cycles shall reset the circuit and force it to wait for the next synchronise signal.

BURST GAP: 12 RF cycles (not sent).

BURST K—INDIFFERENT ELECTRODE COLUMNS 8–10: 20–68 RF cycles to set 3 bits on a binary counter to specify the connection of indifferent electrode columns 8 through 10. Cycles in excess of the maximum 68 cycles shall reset the circuit and force it to wait for the next synchronise signal.

BURST GAP: 12 RF cycles (not sent).

BURST L—AMPLITUDE CHARGING: 12 to 252 RF cycles to charge a capacitor to a known voltage such that it may be passed through a resistor of known value thus providing a known current to be utilized as the control input to a current mirror thus creating a programmable, constant current sink.

BURST M—STIMULUS PHASE 1: As required, real time.

BURST GAP: 12 RF cycles (not sent).

BURST N—STIMULUS PHASE 2: As required, real time, equal in cycle quantity (duration) to STIMULUS PHASE 1 in normal operation.

SEQUENCE_GAP: a delay of a minimum of 4 cycles greater than the packet burst gap. This extended gap resets the circuit in preparation of subsequent sequences.

Each of the 14 bursts (A through N) which comprise a sequence have a range of fixed frequency pulse cycles that are allowable by the protocol. With three exceptions (bursts L, M, and N), all bursts have limitations on their pulse quantity wherein an excess of fixed frequency pulse quantities in a given burst violates the rules of the protocol and thus initiates a remedial action of some form as described above. The duration of burst L indirectly sets the amplitude of the constant current sink by charging a capacitor. As no mechanism exists to prevent the capacitor from being charged to its maximum voltage, nor would such mechanism be desirable, no limit on the duration of burst L physically exists. However, the circuitry of the encoder/transmitter which forms and delivers burst L is not capable of transmitting in excess of 252 cycles; furthermore, as a capacitor is incapable of being charged above the voltage from which it is supplied, the duration of burst L which exceeds that required to fully charge the capacitor would have no effect. Bursts M and N define the duration of the first and second phase of the diphasic stimulus pulse respectively. Neither of these bursts have a physical limit. However, the circuitry of the encoder/transmitter which forms and delivers bursts M and N is not capable of transmitting cycles in excess of 16,320 cycles or 6.5 ms duration when using a carrier frequency of 2.5 MHz.

Figure 5:
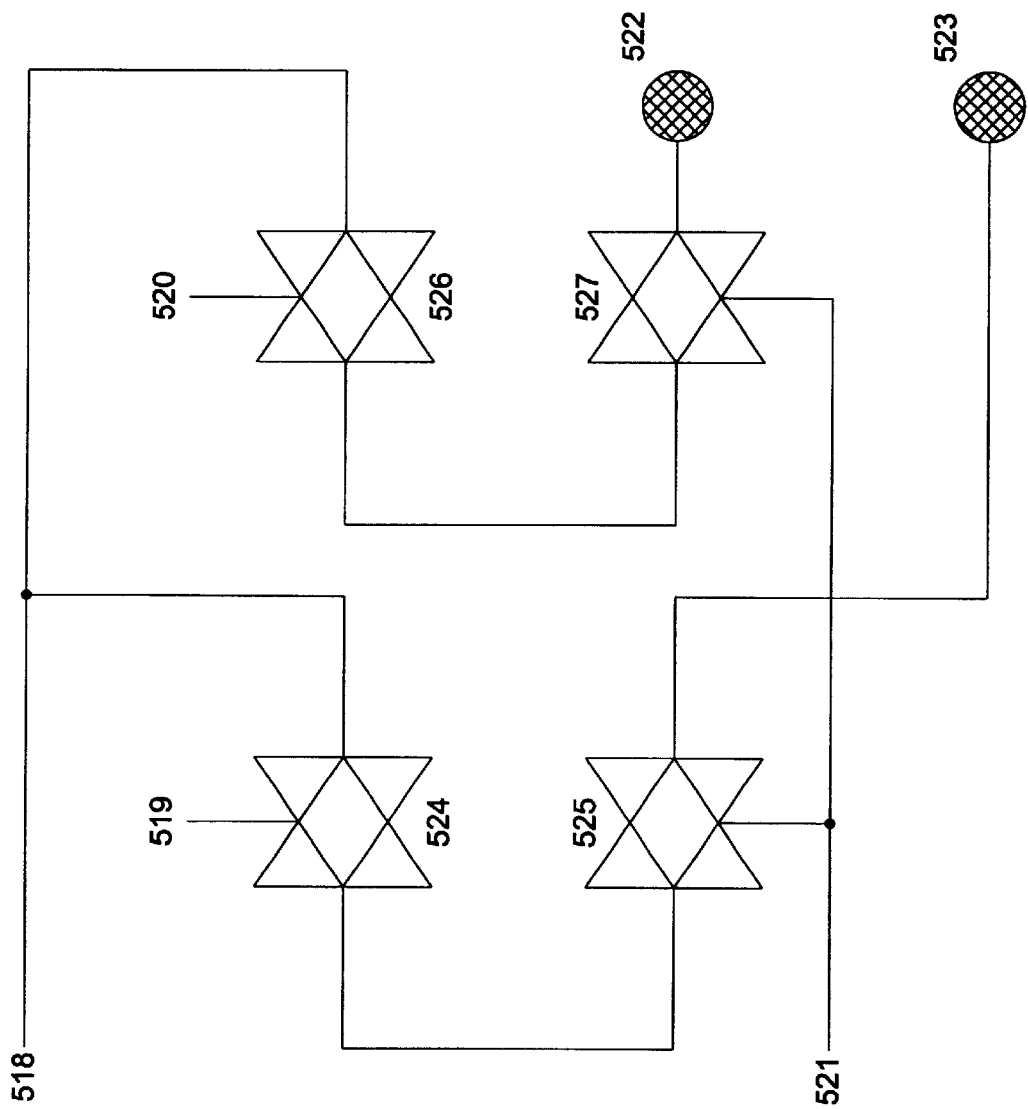
FIG. 5 shows a simplified schematic representation of row/column switching strategy employed in the receiver/decoder/stimulator.
Figure 6A:
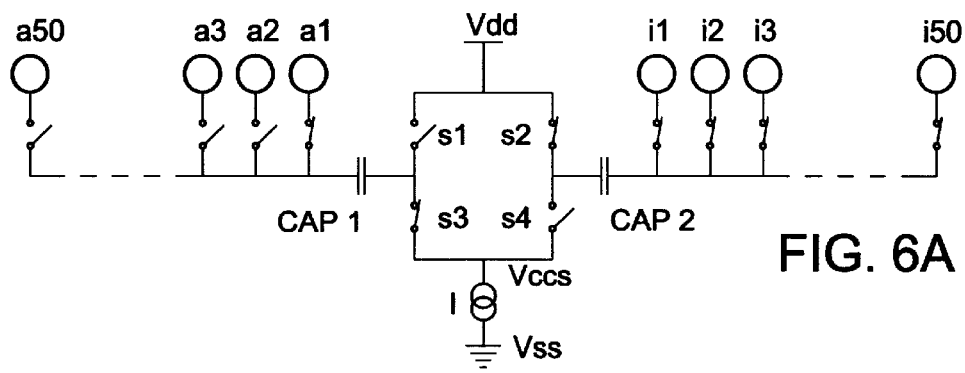
FIG. 6 shows a schematic representation of the switch configuration during the delivery of stimulus and how a single capacitor per electrode block is employed to provide charge balanced stimulus.
Figure 6B:
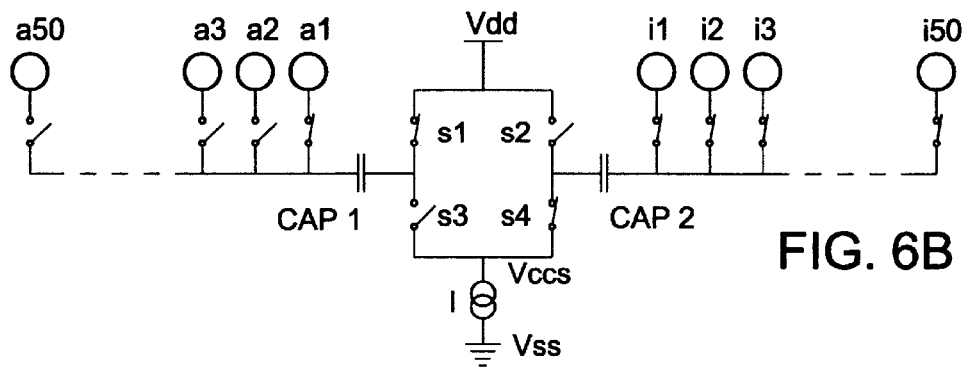
Figure 6C:
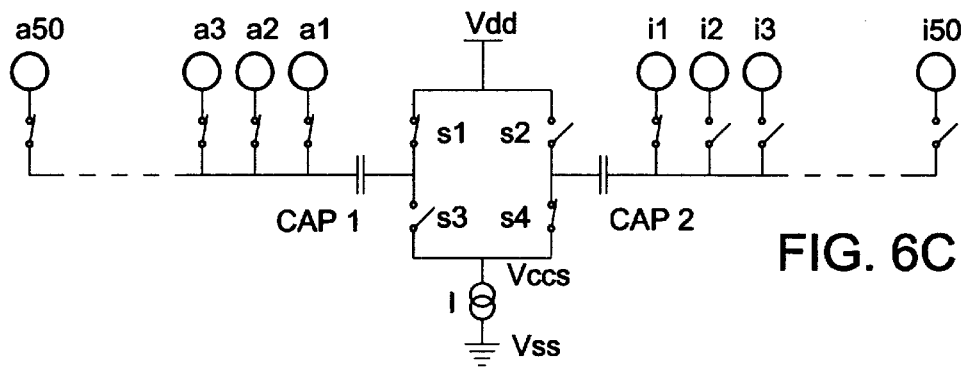
Figure 6D:
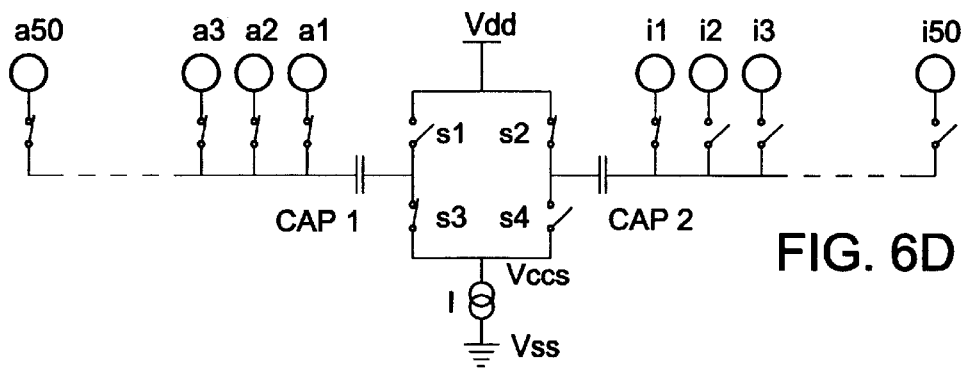

As described above, the data received by the receiver/decoder/stimulator contains specifications for connecting various electrodes to the stimulating circuit using a row/column addressing format. Said row/column format reduces the quantity of data necessary to specify electrodes in comparison to specifying on an individual basis. FIG. 5 shows a simplified schematic for illustration of the row/column addressing technique. 522 and 523 are electrodes that exist on the same addressing row. 518 is the stimulus signal to be passed to the chosen electrode by selectively closing the digitally controlled column switches 524 and 526, and row switches 525 and 527 by evoking the appropriate control signals 519, 520, and 521. An activating signal from 521 closes both row switches 525 and 527 (and all other switches in the row not shown in FIG. 5). An activating signal on 519 would close column switch 524 (and all other switches in the column not shown in FIG. 5), thus connecting signal 518 to electrode 523. Similarly, an activating signal on 520 would close column switch 526 thus connecting signal 518 to electrode 522. An extension of this technique is used to address 100 electrodes in the retinal stimulator wherein two sets, each of 50 electrodes, active and indifferent, are addressed by their respective five rows and ten columns.

Balance of electrical charge when delivering stimulus is critical to the safety and efficacy of the retinal stimulation as charge imbalance is likely to cause electrochemical dissolution of the electrode material and may lead to damage of the retinal tissue. To address the charge balance requirement, the retinal stimulator employs two complementary safeguards against the delivery of net DC current to the stimulating electrodes. These are:

Two stimulus phases, of opposite polarity, matched current magnitude and duration.

Individual capacitors in series with each electrode block (active and indifferent).

FIG. 6 shows these features in various stages of their operation. FIG. 6A shows the switch configuration for delivery of the cathodic phase of the constant current stimulus to active electrode A1 with the return path for the stimulus through all 50 indifferent electrodes. FIG. 6B shows the switch configuration for delivery of the anodic phase of the constant current stimulus through the same electrodes. The switches for routing Vdd and Vccs to the electrode blocks (s2 and s3 in FIG. 6A and s1 and s4 in FIG. 6B) are closed for equal duration thus delivering equal but opposite charge during each of the two phases of stimulus. The capacitor in series with each of the electrode blocks (CAP1 and CAP2 in FIG. 6) further insure charge balance as capacitors do not pass net DC current. FIG. 6C and FIG. 6D show the same stimulation procedure as above with the exception that the roles of the active and indifferent electrode blocks are transposed, achieved by evoking the POLARITY signal of burst J as described above, the effect being to allow for any one of the 100 electrodes to serve as the stimulating electrode whereby the cathodic phase of the diphasic stimulus is passed first therethrough. FIG. 6 shows only one form of return path for the stimulus pulse wherein all indifferent electrodes are connected in parallel, this is not the limiting case, as any one active electrode may be used to deliver stimulus with the return path for the stimulus current being passed through any one or more of the indifferent electrodes.

Said active and indifferent electrodes are implanted on, under or above the retina and held in a geometric pattern of the preferred form shown in FIG. 7. Said geometric pattern, its electrode carrier 702 and associated electrodes (generically identified as 703), are collectively described as an electrode array 701 wherein discreet sites of electrically conducting material form a geometric pattern upon which an image may be mapped by selectively stimulating the individual electrodes, thus evoking a psychophysical response in the patient such that a spot of light is observed in the area upon which a cathodic first, diphasic, electrical stimulus pulse is delivered. Electrode carrier 702 comprises a flexible, elastomeric material wherein recesses for each of the 100 electrode sites exist in an equidistant geometric grid such that electrodes 703 may be situated therein. A preferred embodiment to the electrode array includes a facility for locating one or more electrode site(s) away from the geometric grid, on the external surface of the fixating tack 704 for example, such that it/they may be used as grounding electrode(s) thus facilitating monopolar stimulation wherein stimulus is delivered to one of the electrodes on the geometric grid and the return path for the stimulus is through the remote grounding electrode. Each electrode 703 is electrically connected to the receiver/decoder/stimulator by way of its respective lead wire 705.

Figure 8:
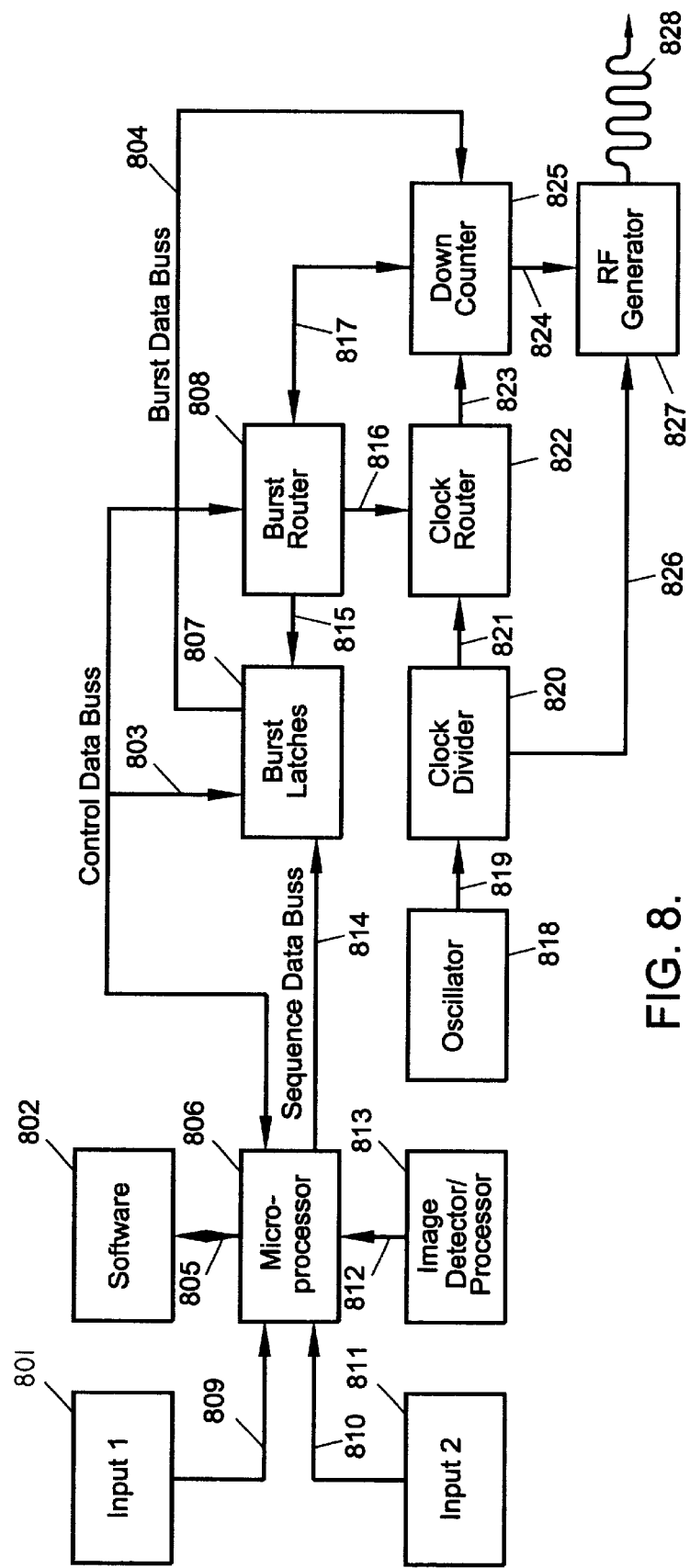
FIG. 8 shows a block diagram of the transmitter circuit.

The block diagram shown in FIG. 8 describes the operation of the external image processor/encoder/transmitter of the retinal stimulator. The image detector/processor 813 comprises a means to obtain an image from the environment and process said image into an array of 100 pixels of varying intensity that correspond to the 100 electrode sites on the implantable electrode array. A preferred method of achieving said image processing is to obtain a virtual image by means of a digital camera and extracting the intensity of discreet regions of said virtual image corresponding to the geometric pattern of the electrode array. Said intensities and their corresponding electrode locations are stored in electronic memory and supplied to the microprocessor 806 by way of data interface 812. Image encoding takes place in the external encoder by way of software 802 and microprocessor 806. Said software requires the following inputs to be made to the microprocessor 806.

| INPUT 1 (801 supplied via interface 809) - MEMORY SPECIFYING: | |
|---|---|
| i. | BURST GAP CYCLES |
| ii. | SEQUENCE GAP CYCLES |
| iii. | STIMULUS PHASE DURATION |
| iv. | STIMULATION STRATEGY |
| INPUT 2 (811 supplied via interface 810) - MEMORY SPECIFYING: | |
| v. | ELECTRODE NUMBER |
| vi. | ROW AND COLUMN ADDRESS |
| vii. | PATIENT THRESHOLD |
| viii. | PATIENT TOLERANCE LIMIT |

For each of the 100 electrodes.

| INPUT 3 (from 813 supplied via interface 812) - MEMORY SPECIFYING: | |
|---|---|
| i. | ELECTRODE NUMBER |
| ii. | INTENSITY (0 OFF, 100 BRIGHTEST) |

For each of the 100 electrodes

The elements of INPUT 1 are specified at system start-up time and used throughout the stimulation session as constant parameters. BURST GAP CYCLES sets the quantity of clock cycles for the silent period that follows all bursts with the exception of burst N of FIG. 4. SEQUENCE GAP CYCLES sets the quantity of clock cycles for the silent period which follows each sequence. The sequence gap follows burst N of FIG. 4. STIMULUS PHASE DURATION sets the quantity of clock cycles for the duration of each of the two stimulus phases of the diphasic pulse. Note that the system is capable of performing similarly had the stimulus amplitude been specified as a constant and the pulse width varied to achieve intensity modality. STIMULATION STRATEGY specifies which method of stimulation is to be utilized during the stimulation session. Strategies include, but are not limited to: bipolar stimulation wherein a single active electrode is stimulated with the return path for stimulus being through a single indifferent electrode; or common ground wherein a single active electrode is stimulated with the return path for stimulus being through all indifferent electrodes in parallel.

INPUT 2 contains ELECTRODE NUMBERS and their unique ROW AND COLUMN ADDRESSes thus providing an indexing relationship wherein a given electrode may be specified by a number rather than its row/column address and vice versa. FIG. 7 shows the indexing relationship whereby a given electrode may be uniquely addressed by a particular row and column specification. Other elements of INPUT 2 are patient and stimulation strategy specific. The PATIENT THRESHOLD and PATIENT TOLERANCE LIMIT are determined empirically through interactive, psychophysical study wherein a clinician assumes conservatively low values for PATIENT THRESHOLD and PATIENT TOLERANCE LIMIT and gradually increases stimulus amplitude until such time as the patient observes a spot of light for the given electrode. The intensity is recorded, in units of amplitude charging cycles, as PATIENT THRESHOLD. Further increasing the stimulus amplitude may eventually reach a point were pain is observed or no further increase in light intensity is observed by the patient. If this point exists, it is recorded, in units of amplitude charging cycles, as the PATIENT TOLERANCE LIMIT, otherwise the PATIENT TOLERANCE LIMIT is recorded as full scale amplitude charging cycles or 252 cycles—the maximum allowable cycles in burst L. The values of INPUT 2 are stored in non volatile memory for use in all stimulus sessions for a given patient.

The INTENSITY elements of INPUT 3 are image specific. A single INTENSITY for each electrode site is specified in INPUT 3 and is scaled in value from 0 to 100 as a result of previous image processing within 813.

The preferred sequence of delivering stimulus to the electrode sites on the array shown in FIG. 7 is to interleaf the rows whereby stimulus is sequentially delivered across the first row, followed by the third, fifth, seventh and ninth rows, then deliver stimulus across the second row, followed by the fourth, sixth, eighth and tenth rows. The preferred method of achieving interleaving is to number the electrodes in accordance with the aforesaid sequence whereby electrodes in row 1 of the array of FIG. 7 are numbered as electrodes 1 through 10; electrodes in row 3 are numbered 11 through 20, and so on to the electrodes of row 9, numbered as 41 through 50. Similarly, electrodes in row 2 of the array are numbered as electrodes 51 through 60; electrodes in row 4 are numbered 61 through 70, and so on to the electrodes of row 10, numbered as 91 through 100. Numbering the electrodes in such a way provides for a means of addressing the electrodes in sequential order while delivering stimulus based upon the data obtained from INPUT 3.

Following the aforesaid numbering scheme, starting with electrode 1, and indexing, one-by-one, to electrode 100, the INPUT 3 data is read via interface 812, evaluated and utilized in the following way by microprocessor 806 and software 802:

i. If the INTENSITY of the present electrode number is zero then skip to viii.

iv. Using INPUT 2 and INPUT 3 data, calculate the quantity of cycles for the Amplitude Charging burst (burst L of FIG. 4.): AMPLITUDE CYCLES= PATIENT THRESHOLD+((PATIENT TOLERANCE LIMIT−PATIENT THRESHOLD)*INTENSITY/100)

iii. Calculate the quantity of cycles required in the remaining bursts described in the data/power protocol to build the sequence. Use INPUT 1 data to establish the quantity of cycles for the Synchronization (A), Phase 1 (M), and Phase 2 (N) bursts, and the Burst and Sequence gaps. A look-up table is used to translate the row/column address contained in INPUT 2 into electrode configuration bursts (B through K) in accordance with the STIMULATION STRATEGY of INPUT 1.

iv. Translate burst and gap cycle quantities into binary format and send to the Sequence Data Buss 814.

v. Wait for completion of previous sequence by continuous polling of a transmitter circuit status signal on the Control Data Buss 803.

vi. Send control signal on the Control Data Buss 803 to load data from the Sequence Data Buss 814 into the Burst Latches 807 to configure the present sequence.

vii. Send control signal on the Control Data Buss 803 to Burst Router 808 to transmit the sequence.

viii If electrode number is 100, skip to x.

ix. Index the electrode number by one and return to i.

x. Obtain new INPUT 3 data from Image Detector/Processor 813, reset electrode number to 1, and return to i.

Sequence data containing binary information defining the cycle quantities for each of the 14 packet bursts and packet burst gap which separates said packet bursts is supplied by the microprocessor on the Sequence Data Buss 814. Said sequence data is asynchronous with the operation of the remainder of the image processor/encoder/transmitter circuit and thus may be placed on the Sequence Data Buss at any time. Upon initial start-up or upon completion of the transmission of a given sequence, a control bit on the Control Data Buss 803 is evoked by Burst Router 808 to alert the microprocessor 806 that the circuit is ready to transmit a new sequence. The microprocessor 806, if complete in its task of supplying the Sequence Data Buss 814 with data defining the next sequence, toggles a control bit on Control Data Buss 803 to load Burst Latches 807. Upon completion of loading the Burst Latches, the microprocessor 806 evokes a transmit signal on Control Data Buss 803 to transmit the sequence. Following the evocation of said transmit signal, the microprocessor 806 and software 802 are free to commence the construction of the next sequence data and place the appropriate signals on Sequence Data Buss 814. Upon receiving the transmit signal, Burst Router 808 instructs Burst Latches 807 to activate the latch containing data for the synchronize packet burst (Burst A of FIG. 4) and place its data on Burst Data Buss 804 thus programming the quantity of cycles to be counted by Down Counter 825. Clock pulses 823 are counted by Down Counter 825 until such time as the clock pulses received match the programmed quantity thus evoking a completion signal to Burst Router 808 via interface 817 indicating that the counting is complete. Said completion signal causes Burst Router 808 to instruct Burst Latches 807 to activate the latch containing data for the packet burst gap and place its data on the Burst Data Buss 804 thus programming the quantity of cycles to be counted by Down Counter 825. Clock pulses 823 are counted by Down Counter 825 until such time as the clock pulses received match the programmed quantity thus evoking a completion signal to Burst Router 808 via interface 817 indicating that the counting is complete. This procedure repeats for the subsequent packet bursts (Bursts B through N of FIG. 4) and their respective packet burst gaps in all cases except Burst N. Upon the completion of Burst N, the completion signal sent to Burst Router 808 by Down Counter 825 via interface 817 causes the evocation of a control bit on the Control Data Buss 803 by Burst Router 808 to alert the microprocessor 806 that the circuit is ready to transmit a new sequence thereby initiating a repetition of the foregoing events for the next sequence.

During the time Down Counter 825 is counting, an enabling signal is sent to RF Generator 827 via interface 824 such that Radio Frequency (RF) signals 828 are transmitted by an oscillating circuit, within 827, tuned to the carrier frequency. Said signals are in synchronization with the carrier frequency clock 826. The signal enabling RF Generator 827 is evoked only when a packet burst is being counted; packet burst gaps contain no RF signals and thus RF Generator 827 is disabled during packet burst gaps.

The quantity of cycles in the packet bursts range from a minimum of three (Burst A) to a maximum of 16,320 (Bursts M and N). In order to minimize the quantity of control lines on Data Busses 804 and 814 while retaining the capability of delivering said cycle quantities, the clock signal 823 supplying Down Counter 825 is an integer division of the oscillator signal 819 delivered from Oscillator 818. Said division takes place in Clock Divider 820 supplying Clock Router 822 with a plurality of clock signals 821. Burst Router 808 specifies which clock signal is to be delivered on 823 by configuring Clock Router 822 via interface 816. Said configuration is based upon the packet burst being transmitted and thus sets the ratio of counting cycles to carrier frequency cycles.

Figure 9:
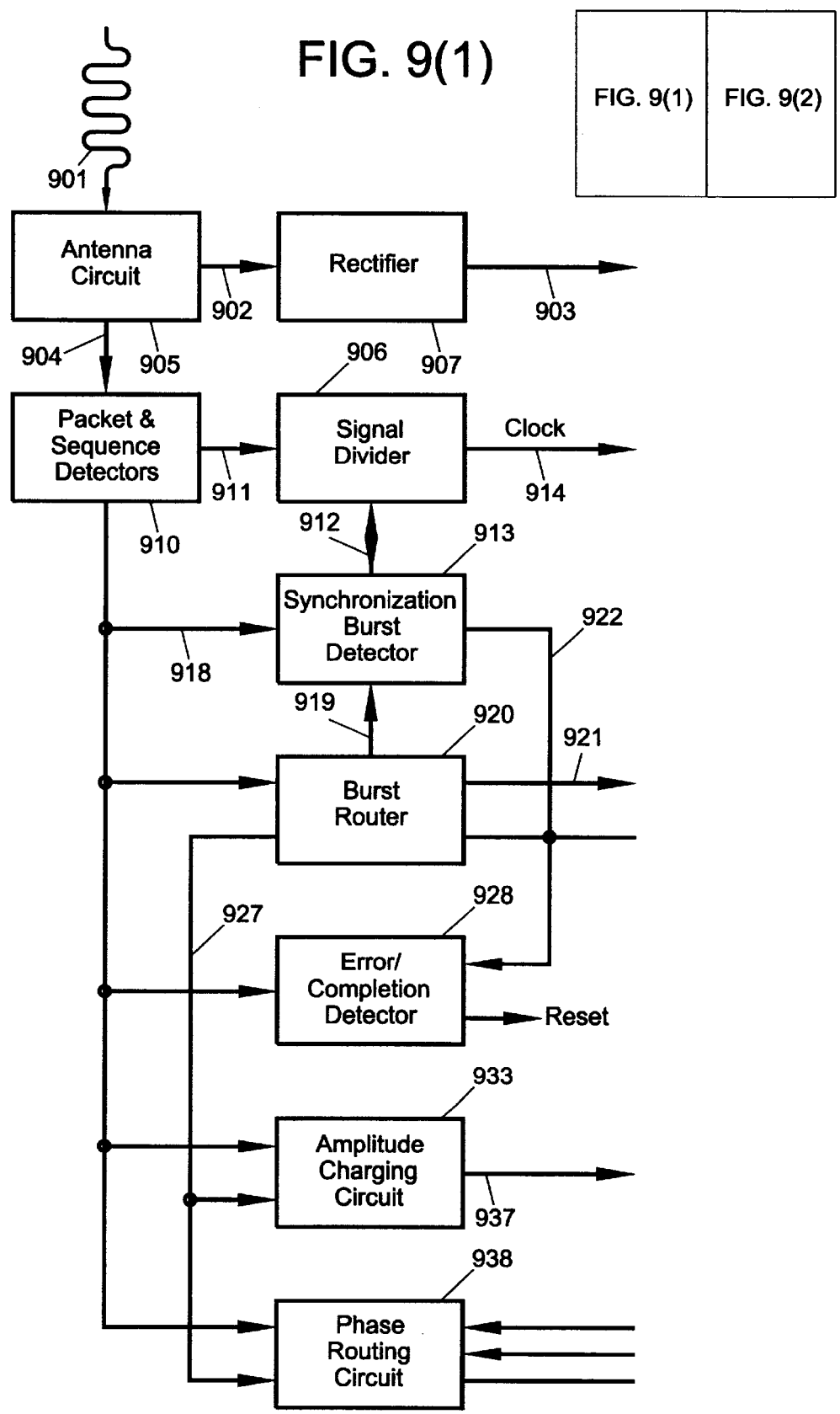
FIG. 9 shows a block diagram of the receiver/decoder/stimulator circuit and components including the hermetic barrier.

The block diagram shown in FIG. 9 describes the operation of the implanted receiver/decoder/stimulator. Radio Frequency (RF) signals 901 are received by Antenna Circuit 905 wherein an oscillating circuit, tuned to the carrier frequency, reconstructs the waveforms transmitted by the external image processor/encoder/transmitter. Said waveforms are passed to Rectifier 907 via interface 902. Rectified signals are passed, via interface 903 to the Power Supply 908 wherein Vdd, the supply voltage for the stimulus pulses, Vref the voltage for the telemetry comparator circuit (described below) and Vlogic, the voltage for driving the digital configuration logic, are regulated and supplied globally to the circuit. The magnitude of Vdd, Vref and Vlogic are with reference to Vss, the lowest potential of the rectified waveform. Signals received by Antenna Circuit 905 are also passed, via interface 904, through Packet and Sequence Detectors 910 then, by way of interface 911, into Signal Divider 906 wherein the quantity of cycles are counted and divided by eight. Within Packet and Sequence Detectors 910, packet burst detection is activated when a packet burst is being received and sequence detection is activated when a sequence is being received (as described above). The Packet Burst and Sequence detection signals are passed to the relevant sub circuits via data buss 918.

Packet burst detection determines which of the 14 packet bursts is being received at a given time. Counting of packet bursts takes place in Burst Router 920 which, in its initial state, evokes a signal on interface 919 such that the Synchronization Burst Detector 913 is activated to receive and verify the synchronization burst (burst A of FIG. 4). In order to be determined by said detector as being valid, said synchronization burst must contain a sufficient quantity of cycles to activate packet detection in 910 and must not contain sufficient quantity to be counted as a one in Signal Divider 906. Until such time as a valid synchronization burst is received, counting of packet bursts in Burst Router 920 does not commence. Each invalid synchronization burst evokes a signal on Error buss 922 that serves to evoke a global Reset signal from Error/Completion Detector 928 such that the entire circuit is again placed in a state wherein it awaits the next valid synchronization burst.

Upon completion of detection of said valid synchronization burst, Burst Router 920 directs, via interface 921, a signal to Row/Column Counters & Polarity circuit 924 to configure Active Electrode Row Buss 925 according to the data contained in burst B. Clock-1 Circuit 915 filters Clock signal 914, delivered from Signal Divider 906, such that the first signal received from 914 during the burst is not allowed to pass to interface 923, effectively subtracting one from the quantity of clock signals received on 914 during the burst. If one or more signals are transmitted to interface 923, said signals are passed to Row/Column Counters and Polarity 924 and serve to configure the data on Active Electrode Row Buss 925. The first of said signals received by 924 shall configure the data on 925 such that active electrode row 1 will be activated and active electrode rows 2 and 3 deactivated during stimulus. The second signal received by 924 shall configure the data on 925 such that active electrode row 2 will be activated and active electrode rows 1 and 3 will be deactivated during stimulus. The third signal received by 924 shall configure the data on 925 such that active electrode rows 1 and 2 will be activated and active electrode row 3 will be deactivated during stimulus. The fourth signal received by 924 shall configure the data on 925 such that active electrode row 3 will be activated and active electrode rows 1 and 2 will be deactivated during stimulus. The fifth signal received by 924 shall configure the data on 925 such that active electrode rows 1 and 3 will be activated and active electrode row 2 will be deactivated during stimulus. The sixth signal received by 924 shall configure the data on 925 such that active electrode rows 2 and 3 will be activated and active electrode row 1 will be deactivated during stimulus. The seventh signal received by 924 shall configure the data on 925 such that active electrodes 1, 2 and 3 are activated during stimulus. An eighth signal received by 924 violates the pre-established protocol whereby the packet burst has exceeded the allowable quantity of cycles. Said violation causes the evocation of a signal by 924 on Error Buss 922 such that the entire circuit shall be reset to its initial state by a global Reset signal evoked by Error/Completion Detector 928.

States wherein a plurality of active electrode rows are activated serve no purpose when the active electrode block is being used as such due to the fact that stimulus is delivered from a single electrode only. However, when the roles of the active and indifferent electrode blocks are transposed by means of evocation of the polarity signal (in burst J), the activation of a plurality of rows serves the purpose of allowing the return path of stimulus to be through a plurality of electrodes.

Subsequent packet bursts (C through K) serve to configure, in a similar binary counting fashion as described in burst B, the remainder of Active Electrode Row Buss 925, Active Electrode Column Buss 926, Indifferent Electrode Row Buss 929 and Indifferent Electrode Column Buss 930. An excess of cycles received during any of these bursts causes the evocation of a signal by 924 on Error Buss 922 such that the entire circuit is reset to its initial state by a global Reset signal evoked by Error/Completion Detector 928.

Active Electrode Row Buss 925, and Active Electrode Column Buss 926 deliver signals to close the appropriate switches within Active Electrode Switching 917 such that Active Electrode 909 is connected, via interface 916, through 917 to the output of Phase Routing Circuit 938, interface buss 932. Similarly, Indifferent Electrode Row Buss 929 and Indifferent Electrode Column Buss 930 deliver signals to close the appropriate switches within Indifferent Electrode Switching 936 such that Indifferent Electrode(s) 940 are connected, via interface 935, through 936 to the output of Phase Routing Circuit 938, interface buss 932.

Burst J, during which part of Indifferent Electrode Column Buss 930 is configured, also contains data to transpose the roles of the active and indifferent electrode blocks by configuring the polarity of Phase Routing Circuit 938 via interface 931 based upon data received by 924. This is achieved by an additional binary digit in the counting circuit associated with Burst J.

The receipt of burst L causes Burst Router 920 to activate Amplitude Charging Circuit 933 such that a voltage may be set on interface 937. Said voltage is determined by way of charging a fixed resistor/capacitor circuit from a regulated voltage for the duration of burst L. Constant Current Sink 934 contains a current mirror with a fixed resistance on the drain of the controlling transistor. Passage of known voltage 937 through said fixed resistance sets the current to be passed by 934, via interface 939, to Phase Routing Circuit 938 during stimulus.

Assuming that the roles of the active and indifferent electrode blocks have not been transposed by the polarity signal contained in burst J, delivery of the cathodic phase of stimulus begins with the detection of burst M by 910. Said detection closes the appropriate switches within 938 (see also s1 through s4 of FIG. 6A) such that Constant Current Sink 934 is connected, via interfaces 939 and 916, interface buss 932 and switches within both 938 and 917, to Active Electrode 909. Indifferent Electrode(s) 940 are connected to Vdd through interface 935, interface buss 932 and switches within both Indifferent Electrode Switching 936 and 938.

The anodic phase of stimulus begins with the detection of burst N by 910. Said detection closes the appropriate switches within 938 (see also s1 through s4 of FIG. 6B) such that Vdd is connected, via interface 916, interface buss 932 and switches within 917, to Active Electrode 909. Indifferent Electrode(s) 940 are connected to Constant Current Sink 934 through interfaces 935 and 939, interface buss 932 and switches within both Indifferent Electrode Switching 936 and 938.

Transposing the role of active and indifferent electrode blocks by activating the polarity signal in burst J reverses the polarity of the stimulus pulse such that electrodes within the active electrode block may be utilized as indifferent electrode(s) and vice versa.

Upon completion of burst N, Burst Router 920 evokes a signal on Error Buss 922 such that Error/Completion Detector 928 activates the global Reset signal thus returning the circuit to its original state wherein it awaits the next valid synchronization burst.

An excess in packet burst gap duration or the presence of a sequence gap evokes a signal from Sequence Detectors within 910, transmitted via interface buss 918, to Error/Completion Detector 928. Said detector (928) evokes a global reset signal to return the circuit to its original state wherein it awaits the next valid synchronization burst. Said reset serves as a safeguard against missing packet burst data and is redundant to that evoked by the completion of burst N under normal operating conditions.

The receiver/decoder/stimulator's usefulness as an investigatory tool is enhanced by the addition of a telemetry system that provides data yielding the impedance through which a given stimulus pulse has been passed. By briefly connecting the power supply of the receiver/decoder/stimulator across Antenna Circuit 905, an energy burst, detectable external to the patient, is transmitted. By generating two energy bursts, the first related in time to the supply voltage (Vdd) and a second related in time to the voltage across the constant current source (which varies with tissue impedance), an external source, such as an oscilloscope may be used to measure tissue impedance according to the formula:

$$R = (Vdd - Vccs)i$$

Where R is the tissue impedance, Vdd is the supply voltage, Vccs is the voltage across the constant current source during stimulus delivery (of the anodic phase) and i is the programmed current.

The time measurement of the detection of said energy bursts associated with the telemetry begins with the falling edge of the second phase of stimulus. This being the case, a sufficient gap between successive stimulus sequences must be provided in order that the response to the energy burst may be detected externally using appropriate hardware. The RF signal from subsequent stimulus sequences would obscure the detection of the spikes and the spikes themselves may interfere with the data signal being delivered. For these reasons, the telemetry is only delivered when a sufficient gap is present between successive stimulus sequences.

Figure 10A:
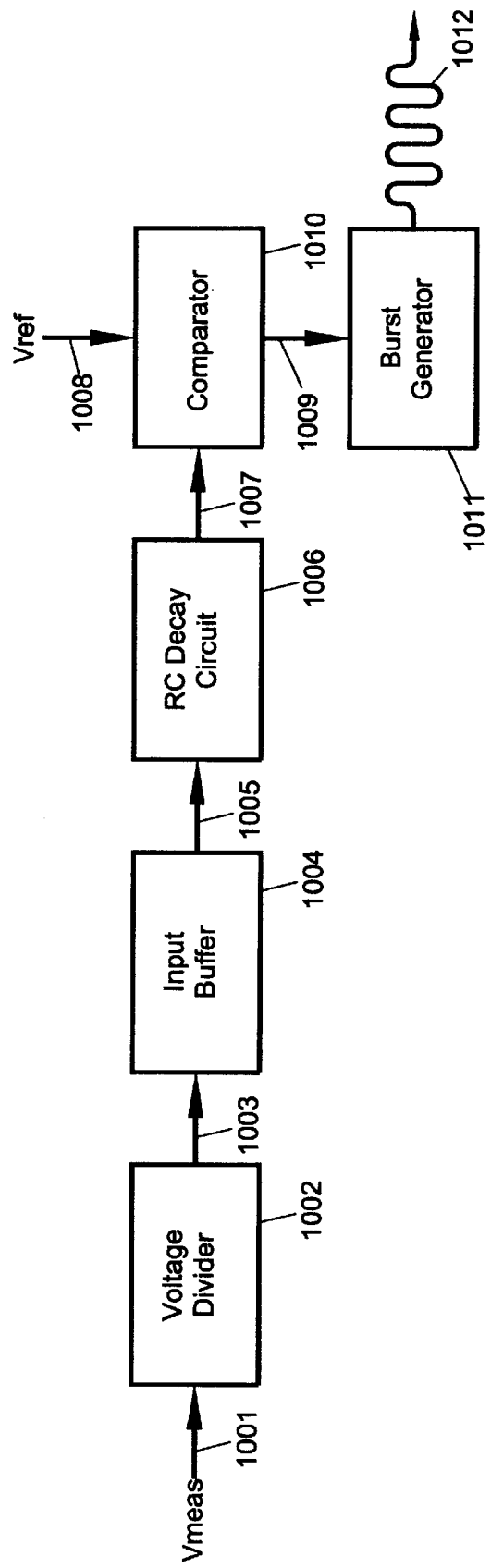
FIG. 10 shows a block diagram representation of the telemetry circuit and a diagram of data transmitted by the receiver/decoder/stimulator during the delivery of telemetry.
Figure 10B:
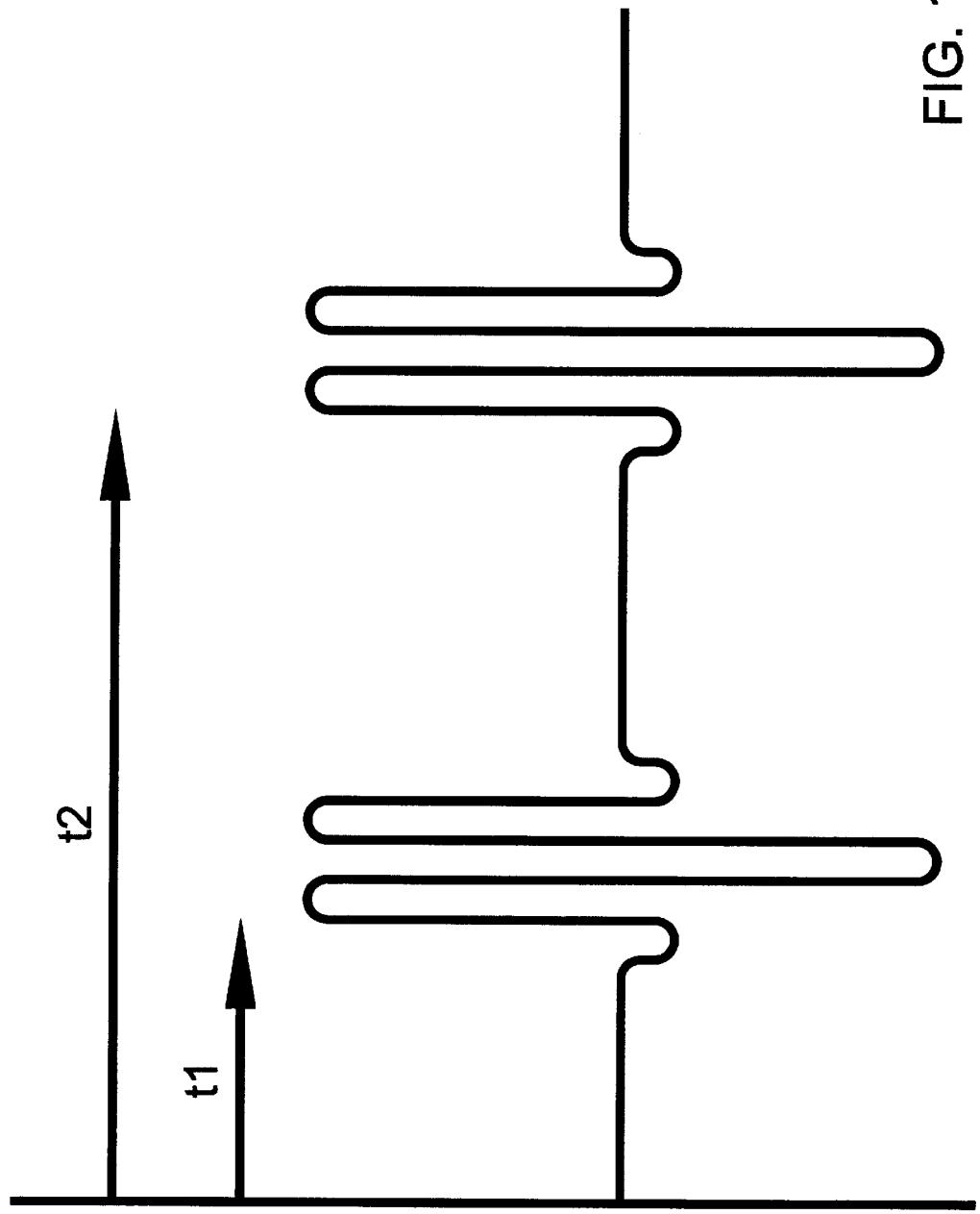

The telemetry circuit, two of which exist, one for Vdd and one for Vccs, is shown in block diagram form in FIG. 10A. Said circuit comprises a voltage divider 1001, buffer 1002, RC decay circuit 1003, comparator 1004 and burst generator 1005. Voltage to be measured (either Vdd or Vccs) is passed through a voltage divider 1001 with a division constant D. Buffer 1002 serves only to isolate the effects of the telemetry circuit on the measured voltage. RC decay circuit 1003, charged during the second phase of stimulus, begins to decay at the falling edge of the second phase of stimulus and decays to a reference voltage, Vref on comparator 1004 at which time an energy burst is generated in 1005. The comparator's slew rate delays the telemetry pulse by a constant ts Thus the formula relating time to voltage becomes:

$$V = D^* \; Vref^* \; \exp((t-ts)/RC)$$

Where t is the time measured from the falling edge of phase two of stimulus to the beginning of the energy burst as shown in FIG 10B.

Figure 11:
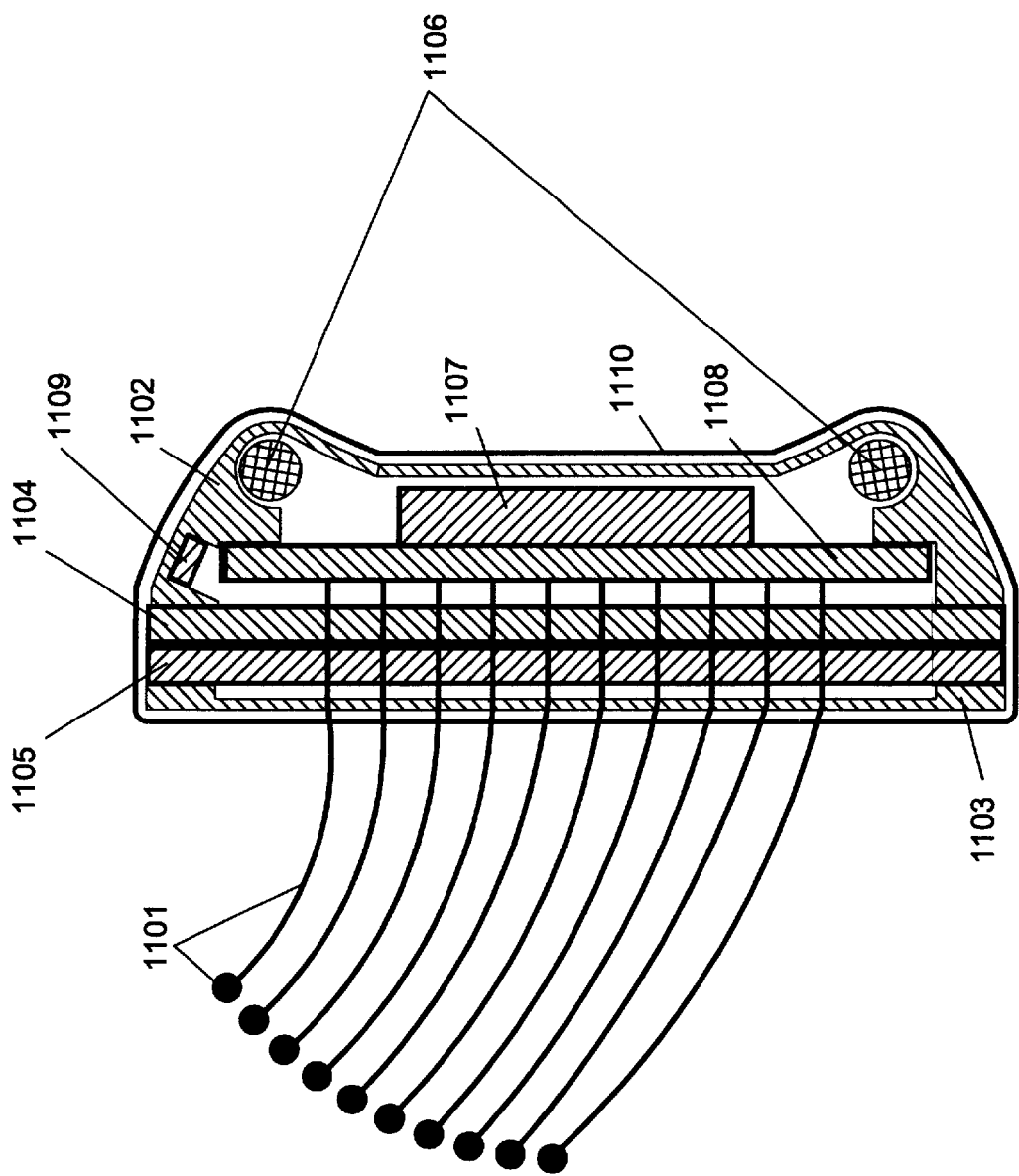
FIG. 11 shows a cross sectional view of the receiver/decoder/stimulator, identifying the components thereof.

The cross sectional view of FIG. 11 shows the components comprising the receiver/decoder/stimulator and one column of electrodes. Said receiver/decoder/stimulator is symmetrical about its central axis and thus is defined in shape by the cross sectional view.

Stimulating electrodes 1101 and alike are fabricated from an appropriate electrical conductor such as platinum wire. The sphere forming the end of said electrode is for the purpose of delivering electrical charge to the retinal ganglion cells. Sphere diameters of said electrodes play a role in the electrical charge density delivered to the stimulation site. As said sphere diameter is of fixed dimension, the charge density is adjusted by the waveform delivered to the stimulation site. An appropriate sphere diameter would fall within the range of about 100–600 m.

The external shell of the receiver/decoder/stimulator comprises two parts, a forward part 1102 and a back part 1103.

The back part 1103 forms a hermetically sealed electrical feed-through insulator fabricated from an appropriate electrical insulating material such as alumina oxide ceramic. In its unfired state, said ceramic is relatively soft thus providing for formation into the required shape and allowing for the passage of a plurality of stimulating electrodes 1101 therethrough. The assembly is fired in a kiln to sinter and shrink the ceramic around the shank of each of the stimulating electrodes 1101 (and alike) thereby forming a hermetic seal. The forward part 1102 is fabricated from a similar insulating material such as alumina oxide ceramic, formed in the unfired state then sintered. Electrical insulating properties of 1102 allow for the unhindered passage of radiofrequency waves. Said forward and back parts 1102 and 1103 are each fitted with a metallic flange 1104 and 1105 respectively by way of attaching said flange to the ceramic by an appropriate means such as brazing using TiCuNi braze material.

Receiving antenna 1106 is fabricated from an appropriate electrical conductor such as copper wire. Said antenna is situated such that it may receive signals from the external image processor/encoder/transmitter. Said receiving antenna 1106 is electrically connected at both ends to electronics 1107. Said electronics comprises power extraction, waveform rectification, voltage supply regulation, purpose built integrated circuits for data decoding, formation and delivery of stimulus and formation and transmission of telemetry as described in the foregoing text. Said electronics are mounted upon circuit board 1108 such that the required electrical connections can be made with antenna 1106, stimulating electrodes 1101 (and alike) and all internal electronic components.

Magnetic attractors 1109 such as rare earth magnets or ferromagnetic materials are placed within a plurality of cavities within forward part 1102 such that complimentary attractors (not shown), located outside the ocular sphere, may be utilized to hold the receiver/decoder/stimulator in place.

Upon completion of assembly and placement of internal components, flanges 1104 and 1105 are bonded together to form a hermetic seal by an appropriate means such as welding with a YAG laser, thus forming a hermetic barrier around the internal components.

The completed assembly or part thereof may be coated by an appropriate material 1110 such as silicone elastomer such that tissue contacting surfaces are biologically inert.

Although the foregoing description of the present invention makes reference to particular embodiments, it is not to be construed as limiting as these embodiments are merely illustrative of the principles of the invention and the application thereof. The invention is defined by the following claims, their equivalents to be included therein.

What is claimed is:

1. A system for stimulating physiologically excitable cells of a retina of an eye to generate a psychophysical response, said system comprising:
   a transmitter for transmitting into the eye, an electromagnetic radio frequency carrier modulated by an encoded visual image signal, and
   an implant within the eye for receiving the modulated carrier and demodulating the encoded visual image signal therefrom, and for decoding the encoded visual image signal and converting the decoded signal into an electrical stimulation signal for delivery to the physiologically excitable cells of the retina to thereby generate the psychophysical response.

2. A system as claimed in claim 1, further comprising an image processor for producing the encoded visual image signal by converting an initial input image into pixel information relating to an array of discreet pixels, each having a particular intensity, and by thereafter encoding said pixel information into said encoded visual image signal.

3. A system as claimed in claim 2, wherein said implant further comprises an array of electrodes for the delivery of the electrical stimulation signal to the physiologically excitable cells of the retina, said array of electrodes being ill corresponding, geometric relationship with the array of discreet pixels associated with the initial input image.

4. A system as claimed in claim 3, wherein the carrier is said modulated by consecutive sequences of discrete data bursts, each of said sequence representing visual image signal parameters including current amplitude and pulse duration for one or more addressed ones of each of said electrodes.

5. A system as claimed in claim 3, wherein the electrical stimulation signal is charge balanced by providing a capacitive element in series with each of an alternate. opposite two groups of said electrodes, and each of said groups delivers the biphasic relationship.

6. A system as claimed in claim 1, wherein said implant further comprises an error detection circuit for preventing the delivery of the electrical stimulation signal, whenever at least a part of said encoded visual image signal violates a pre-determined encoding protocol.

7. A system as claimed in claim 6, wherein said predetermined encoding protocol includes allowable numbers of cycles of the radio frequency carrier.

8. A system as claimed in claim 1, said system further comprising an external telemetry detector, for receiving auxiliary data transmitted from the implant to derive changes in electrical potential, said changes being associated with the electrical stimulation signal.

9. A system as claimed in claim 8, wherein said telemetry detector is configured to controllably enable adjustment of predetermined procedures and parameters associated with the electrical stimulation signal.

10. A system as claimed in claim 1, wherein said implant further comprises means for receiving and rectifying energy from the radio frequency carrier to supply power for said implant.

11. A system as claimed in claim 1, wherein said implant comprises materials incompatible with ocular tissue, said materials being encapsulated within a hermetically sealed ocular compatible chamber.

12. A system as claimed in claim 1, wherein said implant is positioned within the ocular anatomy, at least by way of a magnetic force.

13. A system for stimulating physiologically excitable cells of a retina of an eye, said system comprising:
   an image processor for processing a captured image into an array of discrete pixels, each having a particular intensity,
   an encoder for encoding said array of discrete pixels into an encoded data signal,
   a transmitter for transmitting the encoded data signal in sequential bursts, to a receiver within the eye for receiving the encoded data signal transmitted from the transmitter,
   a decoder within the eye for converting the encoded data signal received by the receiver into stimulus signals, and
   a stimulator within the eye for selectively stimulating the physiologically excitable cells of the retina as a function of the stimulus signals.

14. A system for stimulating physiologically excitable cells of a retina of an eye, said system comprising:
- an image processor for processing a captured image into an array of discreet pixels, each having a particular intensity,
- an encoder for encoding said array of discrete pixels into an encoded data signal,
- a transmitter for transmitting the encoded data signal in sequential bursts to a receiver within the eye for receiving the encoded data signal transmitted from the transmitter,
- a decoder within the eye for converting the encoded data signal received by the receiver into stimulus signals whenever a pre-determined data protocol associated with encoded data signal is satisfied, and
- a stimulator within the eye for selectively stimulating the physiologically excitable cells of the retina as a function of the stimulus signals.

15. A system for stimulating the physiologically excitable cells of a retina of an eye, said system comprising:
- an image processor for processing a captured image into an array of discreet pixels, each having a particular intensity,
- an encoder for encoding said array of discreet pixels into an encoded data signal,
- a transmitter for transmitting the encoded data signal in sequential bursts to a receiver within the eye for receiving the encoded data signal transmitted from the transmitter,
- a decoder within the eye for converting'the encoded data signal received by the receiver into stimulus signals, and
- a stimulator within the eye for selectively stimulating the physiologically excitable cells of the retina as a function of the stimulus signals and for charge balancing said stimulation signal by grouping each of said electrodes into two or more groups and providing each group with a series arranged capacitive element.

16. A retinal stimulation system for use in a patient, said system comprising:
- an implant for receiving power and configuration data transmitted by an external device having the ability to process, encode and transmit an external image,
- an external telemetry detector for receiving data from said implant and for deriving a change in electrical potential across the stimulation circuit, and
- an external processor for controlling adjusting the image processing procedure and stimulus parameters of the implant.

17. An eye implant for stimulating a retina of an eye to generate a psychophysical response, said implant comprising:
- a receiver for receiving an electromagnetic radio frequency carrier modulated by an encoded visual image signal, and for demodulating the encoded visual image signal therefrom,
- a decoder for converting the encoded visual image signal into stimulus signals, and
- a stimulator for selectively stimulating the retina as a function of the stimulus signals.

18. A method of enabling a phosphene to be produced, in response to stimulation of nerve cells in a being, said method comprising the steps of:
- obtaining and dividing a visual image into an array of discrete regions,
- extracting visually related intensity data for each of said discrete regions,
- producing a sequence of encoded image data comprising at least, said intensity data and a unique address for each of said regions,
- transmitting said encoded image data over a tuned inductive link,
- receiving and decoding said image data into a plurality of stimulus signals having both position and intensity attributes, and
- applying said stimulus signals to nerve cells which are capable of producing the phosphene.

19. A method of stimulating a retina of an eye to generate a psychophysical response, said method comprising the steps of:
- transmitting an electromagnetic radio frequency carrier modulated by an encoded visual image signal into the eye; and
- within the eye, receiving the modulated carrier, demodulating the encoded visual image signal therefrom, decoding the encoded visual image signal, converting the decoded signal into an electrical stimulation signal and delivering the electrical stimulation signal to the retina to thereby generate the psychophysical response.

20. A method of stimulating a retina of an eye to generate a psychophysical response, said method comprising the steps of:
- processing a captured image into an array of discrete pixels, each having a particular intensity,
- encoding said array of discrete pixels into an encoded data signal;
- transmitting the encoded data signal in sequential bursts, to a receiver within the eye,
- receiving the encoded data signal by said receiver and converting the encoded data signal into stimulus signals; and
- selectively stimulating the retina as a function of the stimulus signals.

* * * * *